(12) United States Patent
Baeumner

(10) Patent No.: US 7,718,388 B2
(45) Date of Patent: May 18, 2010

(54) UNIVERSAL BIOSENSOR AND METHODS OF USE

(75) Inventor: Antje J. Baeumner, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 11/595,480

(22) Filed: Nov. 10, 2006

(65) Prior Publication Data

US 2010/0068696 A1    Mar. 18, 2010

Related U.S. Application Data

(63) Continuation of application No. 10/449,369, filed on May 30, 2003, now abandoned.

(60) Provisional application No. 60/385,146, filed on May 31, 2002.

(51) Int. Cl.
| | | |
|---|---|---|
| C12Q 1/00 | (2006.01) | |
| C12Q 1/06 | (2006.01) | |
| G01N 33/00 | (2006.01) | |
| G01N 33/53 | (2006.01) | |

(52) U.S. Cl. ............ 435/7.95; 435/4; 435/7.1; 435/7.92; 435/7.94; 435/39; 435/287.1; 435/287.2; 436/501; 436/536; 436/538; 436/540

(58) Field of Classification Search .......... 435/4, 435/5, 6, 7.1, 7.2, 7.4, 7.5, 7.8, 7.9, 7.92, 435/7.93, 7.94, 7.95, 39, 287.1, 287.2; 436/43, 436/44, 46, 164, 169, 172, 174, 501, 512, 436/513, 518, 523, 536

See application file for complete search history.

(56) References Cited

U.S. PATENT DOCUMENTS

| | | |
|---|---|---|
| 4,048,298 A | 9/1977 | Niswender |
| 4,172,770 A | 10/1979 | Semersky et al. |
| 4,225,410 A | 9/1980 | Pace |
| 4,235,601 A | 11/1980 | Deutsch et al. |
| 4,517,288 A | 5/1985 | Giegel et al. |
| 4,517,303 A | 5/1985 | Freytag et al. |
| 4,571,543 A | 2/1986 | Raymond et al. |
| 4,594,327 A | 6/1986 | Zuk |
| 4,605,630 A | 8/1986 | Kung et al. |
| 4,636,479 A | 1/1987 | Martin et al. |
| 4,668,619 A | 5/1987 | Greenquist et al. |
| 4,695,554 A | 9/1987 | O'Connell et al. |
| 4,703,017 A | 10/1987 | Campbell et al. |
| 4,708,933 A | 11/1987 | Huang et al. |
| 4,752,572 A | 6/1988 | Sundberg et al. |
| 4,806,311 A | 2/1989 | Greenquist |
| 4,822,566 A | 4/1989 | Newman |
| 4,855,240 A | 8/1989 | Rosenstein et al. |
| 4,874,710 A | 10/1989 | Piran |
| 4,880,635 A | 11/1989 | Janoff et al. |
| 4,916,080 A | 4/1990 | Imai et al. |
| 4,920,046 A | 4/1990 | McFarland et al. |
| 4,939,098 A | 7/1990 | Suzuki et al. |
| 5,001,048 A | 3/1991 | Taylor et al. |
| 5,006,473 A | 4/1991 | Bouma et al. |
| 5,045,285 A | 9/1991 | Kolesar, Jr. |
| 5,047,245 A | 9/1991 | Bally et al. |
| 5,081,013 A | 1/1992 | Rovelli et al. |
| 5,085,987 A | 2/1992 | Olson |
| 5,089,181 A | 2/1992 | Hauser |
| 5,096,629 A | 3/1992 | Nanba et al. |
| 5,130,257 A | 7/1992 | Baer et al. |
| 5,141,751 A | 8/1992 | Tomikawa et al. |
| 5,141,868 A | 8/1992 | Shanks et al. |
| 5,155,022 A | 10/1992 | Naqui et al. |
| 5,169,789 A | 12/1992 | Bernstein |
| 5,173,406 A | 12/1992 | Hosoda et al. |
| 5,194,133 A | 3/1993 | Clark et al. |
| 5,198,367 A | 3/1993 | Aizawa et al. |

(Continued)

FOREIGN PATENT DOCUMENTS

EP         0 239 318 A1    9/1987

(Continued)

OTHER PUBLICATIONS

Allen et al., "A Noninstrumented Quantitive Test System and Its Application for Determining Cholesterol Concentration in Whole Blood," *Clin. Chem.* 36:1591-1597 (1990).
"Analytical Operations for the Detection of mRNA" (Jan. 2002).
Armbruster et al., "Screening for Drugs of Abuse with the Roche ONTRAK Assays," *J. Anal. Tox.* 16:172-175 (1992).
Ausborn et al., "The Protective Effect of Free and Membrane-bound Cryprotectants During Freezing and Freeze-drying of Liposomes," *J. Controlled Release* 30:105-116 (1994).
Babbitt et al., "Contact-dependent, Immunecomplex-mediated Lysis of Hapten-sensitized Liposomes," *Bioconjugat Chem.* 4:199-205 (1993).
Baeumner, A.J., "Bioanalytical Microsystems: Approaching Single Cell Level Detection of Pathogenic Bacteria and Viruses," *Bioanalytical Microsystems and Biosensors Lab*, Department of Biological and Enviornmental Engineering Cornell University, Ithaca, New York (Nov. 22, 2002).

(Continued)

*Primary Examiner*—Mark Navarro
*Assistant Examiner*—JaNa Hines
(74) *Attorney, Agent, or Firm*—Nixon Peabody LLP

(57) ABSTRACT

The present invention relates to methods for detecting or quantifying an analyte in a test sample including providing at least one test mixture including a test sample, at least one marker complex, wherein each marker complex includes a particle, a marker, and one member of a coupling group, a first binding material selected to bind to a portion of the analyte, a second binding material selected to bind with a portion of the analyte other than the portion of the analyte for which the first binding material is selected, analyte analog, and/or marker conjugate. The at least one test mixture is passed through a membrane. The amount of marker on the membrane is detected and correlated to the presence or amount of analyte in the test sample.

23 Claims, 13 Drawing Sheets

U.S. PATENT DOCUMENTS

| | | | |
|---|---|---|---|
| 5,200,051 A | 4/1993 | Cozzette et al. | |
| 5,208,143 A | 5/1993 | Henderson et al. | |
| 5,248,590 A | 9/1993 | Rutner et al. | |
| 5,284,748 A * | 2/1994 | Mroczkowski et al. | 435/6 |
| 5,308,775 A | 5/1994 | Donovan et al. | |
| 5,310,650 A | 5/1994 | McMahon et al. | |
| 5,312,762 A | 5/1994 | Guiseppi-Elie | |
| 5,340,716 A | 8/1994 | Ullman et al. | |
| 5,346,832 A | 9/1994 | Aizawa et al. | |
| 5,354,692 A | 10/1994 | Yang et al. | |
| 5,369,036 A | 11/1994 | Mercolino et al. | |
| 5,384,264 A | 1/1995 | Chen et al. | |
| 5,389,523 A | 2/1995 | Plant et al. | |
| 5,393,527 A | 2/1995 | Malick et al. | |
| 5,399,500 A | 3/1995 | Oppenheimer et al. | |
| 5,416,214 A | 5/1995 | Pease et al. | |
| 5,459,041 A | 10/1995 | Blaser et al. | |
| 5,491,097 A | 2/1996 | Ribi et al. | |
| 5,494,803 A | 2/1996 | Carbonell et al. | |
| 5,498,551 A | 3/1996 | De Jaeger et al. | |
| 5,501,949 A * | 3/1996 | Marshall | 435/6 |
| 5,516,638 A | 5/1996 | Urnovitz et al. | |
| 5,529,902 A | 6/1996 | Kottke et al. | |
| 5,532,133 A | 7/1996 | Barnwell | |
| 5,567,591 A | 10/1996 | Lovell et al. | |
| 5,591,645 A | 1/1997 | Rosenstein | |
| 5,635,357 A | 6/1997 | Malick et al. | |
| 5,665,552 A | 9/1997 | Maret et al. | |
| 5,670,328 A | 9/1997 | Inoue et al. | |
| 5,672,478 A | 9/1997 | Singh et al. | |
| 5,712,170 A | 1/1998 | Kouvonen et al. | |
| 5,738,868 A | 4/1998 | Shinkarenko | |
| 5,753,519 A | 5/1998 | Durst et al. | |
| 5,756,362 A | 5/1998 | Durst et al. | |
| 5,756,879 A | 5/1998 | Yamagishi et al. | |
| 5,766,961 A | 6/1998 | Pawlak et al. | |
| 5,769,080 A | 6/1998 | Unger et al. | |
| 5,770,460 A | 6/1998 | Pawlak et al. | |
| 5,776,487 A | 7/1998 | Maxfield Wilson et al. | |
| 5,780,010 A | 7/1998 | Lanza et al. | |
| 5,789,154 A | 8/1998 | Durst et al. | |
| 5,817,334 A | 10/1998 | Schmidt et al. | |
| 5,863,538 A | 1/1999 | Thorpe et al. | |
| 5,948,624 A | 9/1999 | Rothschild et al. | |
| 5,958,791 A * | 9/1999 | Roberts et al. | 436/514 |
| 6,004,442 A | 12/1999 | Choulga et al. | |
| 6,040,195 A | 3/2000 | Carroll et al. | |
| 6,086,748 A | 7/2000 | Durst et al. | |
| 6,103,127 A | 8/2000 | Pourfarzaneh | |
| 6,159,745 A * | 12/2000 | Roberts et al. | 436/514 |
| 6,248,596 B1 | 6/2001 | Durst et al. | |
| 6,261,535 B1 | 7/2001 | Thorpe et al. | |
| 6,358,752 B1 | 3/2002 | Durst et al. | |
| 6,395,517 B1 | 5/2002 | Abbaszadegan et al. | |
| 6,576,460 B1 | 6/2003 | Baeumner et al. | |
| 2002/0102581 A1 | 8/2002 | Hageman et al. | |
| 2003/0162198 A1 | 8/2003 | Rothschild et al. | |

FOREIGN PATENT DOCUMENTS

| | | |
|---|---|---|
| EP | 0 276 165 A1 | 7/1988 |
| EP | 0 387 696 A2 | 9/1990 |
| EP | 0 402 917 B1 | 12/1990 |
| EP | 0 437 092 A1 | 7/1991 |
| GB | 2 204 398 A | 11/1988 |
| JP | 2308800 | 12/1990 |
| JP | 3267000 | 11/1991 |
| JP | P4135497 | 5/1992 |
| JP | P4286957 | 10/1992 |
| WO | WO 88/04431 | 6/1988 |
| WO | WO 90/02334 | 3/1990 |
| WO | WO 94/03809 | 2/1994 |
| WO | WO 96/24062 | 8/1996 |
| WO | EP 0276165 * | 1/1998 |
| WO | WO 98/36736 | 2/1998 |
| WO | WO 99/60399 | 11/1999 |
| WO | WO 00/72019 A2 | 11/2000 |
| WO | WO 00/79283 | 12/2000 |
| WO | WO 2005/084404 A2 | 9/2005 |

OTHER PUBLICATIONS

Baeumner, A.J., "Bioanalytical Microsystems: Approaching Single Cell Level Detection of Pathogenic Bacteria and Viruses," *Bioanalytical Microsystems and Biosensors Lab*, Department of Biological and Environmental Engineering, Cornell University, Ithaca, New York (Jan. 13, 2003).

Baeumner, A.J., "Bioanalytical Microsystems: Approaching Single Cell Level Detection of Pathogenic Bacteria and Viruses," *Environmental Quality Systems Symposium*, Syracuse, New York (Oct. 28-29, 2002).

Baeumner, A.J., "Bioanalytical Microsystems and Biosensors Based on Molecular Principles," *Bioanalytical Microsystems and Biosensors*, Cornell University, Ithaca, New York (Jan. 20, 2002).

Baeumner, A.J., "Bioanalytical Microsystems and Biosensors for the Detection of Pathogenic Organisms," *Bioanalytical Microsystems and Biosensors Lab*, Department of Biological and Environmental Engineering, Cornell University, Ithaca, New York (Apr. 16, 2002).

Baeumner, A.J.; "Bioanalytical Microsystems and Biosensors for the Detection of Pathogenic Organisms" *Bioanalytical Microsystems and Biosensors Lab*, Department of Biological and Environmental Engineering, Cornell University, Ithaca, New York (Apr. 25, 2002).

Baeumner, A.J., "Bioanalytical Microsystems and Biosensors for the Detection of Pathogenic Organisms," *Bioanalytical Microsystems and Biosensors Lab*, Department of Biological and Environmental Engineering, Cornell University, Ithaca, New York (May 2, 2002).

Baeumner, A.J., "Bioanalytical Microsystems for the Detection of Pathogenic Organisms," *18th Annual International Conference on Contaminated Soils*, Sediments and Water Conference, Amherst, Massachusetts (Oct. 24, 2002).

Baeumner, A.J., "Bioanalytical Microsystems for the Detection of Pathogenic Organisms," *Bioanalytical Microsystems and Biosensors Lab*, Department of Biological and Environmental Engineering, Cornell University, Ithaca, New York (May 2002).

Baeumner, A.J., "Bioanalytical Microsystems for the Detection of Pathogenic Organisms," *Bioanalytical Microsystems and Biosensors Lab*, Department of Biological and Environmental Engineering, Cornell University, Ithaca, New York (Jul. 2002).

Baeumner, A.J., "Bioanalytical Microsystems for the Detection of Pathogenic Organisms," *Bioanalytical Microsystems and Biosensors Lab*, Department of Biological and Environmental Engineering, Cornell University, Ithaca, New York (Aug. 2002).

Baeumner, A.J., "Bioanalytical Microsystems for the Detection of Pathogenic Organisms," *Bioanalytical Microsystems and Biosensors Lab*, Department of Biological and Environmental Engineering, Cornell University, Ithaca, New York (Sep. 2002).

Baeumner, A.J., "Bioanalytical Microsystems for the Detection of Pathogenic Organisms," *Bioanalytical Microsystems and Biosensors Lab*, Department of Biological and Environmental Engineering, Cornell University, Ithaca, New York (Oct. 31, 2002).

Baeumner, A.J., "Biosensing Systems for the Viable Pathogenic Organism Detection," Cornell University, Ithaca, New York (Sep. 13, 2000).

Baeumner, A.J., "Biosensing Systems for the Viable Pathogenic Organism Detection," Cornell University, Ithaca, New York (Mar. 2001).

Baeumner, A.J., "Biosensing Systems for Viable Pathogenic Organism Detection and Their Future," Cornell University, Ithaca, New York (Jul. 12, 2000).

Baeumner, A.J., "Biosensors and Bioanalytical Microsystems for Food Safety," *PITTCON*, Cornell University, Ithaca, New York (Mar. 2002).

Baeumner, A.J., "Biosensors and Bioanalytical Microsystems for the Detection of Viable Pathogenic Organisms," Cornell University, Ithaca, New York (Feb. 25, 2002).

Baeumner, A.J., "Biosensors for Pathogen Detection," *Biosensors and Bioanalytical Microsystems Lab*, Department of Biological and Environmental Engineering, Cornell University, Ithaca, New York (Feb. 2003).

Baeumner, A.J., "Biosensors for Pathogen Detection," *Biosensors and Bioanalytical Microsystems Lab*, Department of Biological and Environmental Engineering, Cornell University, Ithaca, New York (Mar. 19, 2003).

Baeumner, A.J., "Biosensors for Variable Pathogenic Organism Detection," Cornell University, Ithaca, New York (Aug. 2000).

Baeumner, A.J., "Development of Microfluidic Biosensor Devices Based on Liposome Amplification Strategies," CNF Project No. 802-99, Department of Biological and Environmental Engineering, Cornell University, Ithaca, New York (Jun. 2002) (pictorial report).

Baeumner, A.J., "Development of Microfluidic Biosensor Devices Based on Liposome Amplification Strategies," CNF Project No. 802-99, Department of Biological and Environmental Engineering, Cornell University, Ithaca, New York (Jun. 2002) (status report).

Baeumner, A.J., "Nano-biosensors for Sensing, Monitoring and Control in Agriculture and Food Systems," *Bioanalytical Microsystems and Biosensors Lab*, Department of Biological and Environmental Engineering, Cornell University, Ithaca, New York (Nov. 18-19, 2002).

Baumner et al., "Bioanalytical Microsystems for the Detection of Dengue Virus," *Bioanalytical Microsystems and Biosensors Lab*, Department of Biological and Environmental Engineering, Cornell University, Ithaca, New York (Jun. 24, 2002).

Beaumner et al., "Creating a Safre World. Revolutionary Advances in Biosensor Technology," *Biosensors and Bioanalytical Microsystems Lab*, Department of Biological & Environmental Engineering, Cornell University, Ithaca, New York (Apr. 2002).

Beaumner et al., "Creating a Safre World. Revolutionary Advances in Biosensor Technology," *Biosensors and Bioanalytical Microsystems Lab*, Department of Biological and Environmental Engineering, Cornell University, Ithaca, New York (Sep. 2002).

Baeumner et al., "Rapid Multi-analyte Biosensor for the Detection of Four Dengue Virus Serotypes," Cornell University, Ithaca, New York (Apr. 2002).

Collard-Bovy et al., "Microparticle-enhanced Nephelometric Immunoassay. 1. Measurement of $\alpha_s$-Casien and $\alpha$-Casein," *J. Dairy Sci.* 74:3695-3701 (1991).

Connelly & Baeumner, "Design, Fabrication, and Testing of a Portable Microfluidic Device for Nucleic Acid Sequence-based Amplification," *Bioanalytical Microsystems and Biosensors*, Department of Biological and Environmental Engineering, Cornell University, Ithaca, New York (Apr. 8, 2003).

Crowe et al., "Preservation of Freeze-dried Liposomes by Trehalose," *Arch. Biochem. Biophys.* 242:240-247 (1985).

Crowe et al., "Preservation of Liposomes by Freezing-drying," *Liposome Technology*, Gregoriadis, ed., CRC Press, Boca Raton, pp. 229-252 (1993).

Durst, "Automated Analyzer for the Determination of Potassium and Sodium in Whole Blood," *Clinical Chimica Acta* 80:225-234 (1977).

Durst, "Developmental of a Liposome-enhanced Assay Format for the Detection of Specific Nucleic Acid Sequences," Cornell Center for Advanced Technology—Biotechnology Program, Research Directory (1994-1995) (abstract).

Durst et al., "Automated Liposome-based Flow Injection Immunoassay System," *GBF Mono.* 14:181-190 (1990).

Durst et al., "Chemically Modified Electrode for Liposome-mediated Homogeneous Immunoassay," $5^{th}$ *Symposium on Ion-selective Electrodes*, Pergamon Press, Oxford (1989).

Durst et al., "Development of Liposome-enhanced Immuno-biosensing Devices for Field Measurements of Toxic Substances," $2^{nd}$ *Bioelectroanalytical Symposium*, Mátrafüred, Akadémiai Kiadó, Budapest (1992).

Durst et al., "Immunosensor for Extra-lab Measurements Based on Liposome Amplification and Capillary Migration," *Biosensors & Bioelectronics* 8:xiii-xv (1993).

Durst et al., "Organic Electrochemical Techniques Having Potential Clinical Application," *Clin. Chem.* 28:1922-1930 (1982).

Goral et al., "Bioanalytical Microsystems: Approaching Single Cell Level Detection of Pathogenic Bacteria and Viruses," *Bioanalytical Microsystems and Biosensors Lab*, Department of Biological and Environmental Engineering, Cornell University (Sep. 8, 2003).

Harrigan et al., "Protection of Liposomes During Dehydration of Freezing," *Chem. Phys. Lipids* 52:139-149 (1990).

Heath-Fracica et al., "Evaluation of a New Latex Agglutination Test for Detection of Streptococcal Antibodies," *Diagn. Microbiol. Infect. Dis.* 8:25-30 (1987).

Ho et al., "Interactions of Target-sensitive Immunoliposomes with Herpes Simplex Virus," *J. Biol. Chem.* 262(29):13979-13984 (1987).

Hoffman & Baeumner, "Development of a Portable Data Acquisition Unit for a Micro-total Analysis System," Department of Biological & Environmental Engineering, Cornell University, Ithaca, New York (Feb. 2003).

Kannuck et al., "Measurement of Liposome-released Ferrocyanide by a Dual-function polymer Modified Electrode," *Anal. Chem.* 60:142-147 (1988).

Kung et al., "Large Liposome Agglutinaton Technique for the Serological Detection of Syphilis," *J. Immunol. Meth.* 90:189-196 (1986).

Kwakye, S., "Channel Analysis," *ABEN 685 Presentation* (May 19, 2000).

Kwakye, S., *IBE* (Jan. 2002) (poster).

Kwakye, S., *IBE* (Jan. 2002) (introduction).

Kwakye, S., "MicroTAS," *IBE* (Mar. 31, 2001) (poster).

Kwakye & Baeumner, "An Integrated Micro-total Analysis System Based on Nucleic Acid Sequence Recognition," *Department of Agriculture and Biological Engineering*, Cornell University, Ithaca, New York (Mar. 31, 2001).

Kwakye & Baeumner, "Capture and Detection of Pathogelnic RNA in a Microfluidic Device," *Biological & Environmental Engineering* (Mar. 29, 2002).

Kwakye & Baeumner, "Micro-system for Nucleic Acid Based Pathogen Detection," Cornell University, Ithaca, New York (Mar. 25, 2003).

Kwakye & Baeumner, "μTAS Based on Nucleic Acid Sequence Recognition. Concepts and Design" $5^{th}$ *CNF Annual Meeting* (Sep. 14, 2000) (poster).

Locascio-Brown et al., "Liposome Flow Injection Immunoassay: Implications for Sensitivity, Dynamic Range, and Antibody Regeneration," *Anal. Chem.* 2587-93 (1990).

Losso et al., "Development of a Particle Concentration Fluorescence Immunoassay for the Quantitative Determination of IgG in Bovine Milk," *J. Agric. Food Chem.* 41:682-686 (1993).

Lou et al., "One-step Competitive Immunochromatographic Assay for Semiquantitative Determination of Determination of Lipoprotein(a) in Plasma," *Ciin. Chem.* 39:619-624 (1993).

Madden et al, "Protection of Large Unilamellar Vesicles by Trehalose During Dehydration: Retention of Vesicle Contents," *Biochim. Biophys. Acta* 817:67-74 (1985).

Martorell et al., "Liposome Dehydration on Nitrocellulose and Its Application in a Biotin Immunoassay," *Anal. Biachem.* 271:177-185 (1999).

Monroe, "Novel Liposome Immunoassays for Detecting Antigens, Antibodies and Haptens," *J. Liposome Res.* 1:339-337 (1989-90).

Murray et al., "Chemically Modified Electrodes Molecular Design for Electroanalysis," *Anal. Chem.* 59:379A-390A (1987).

Min & Baeumner, "Characteristics of Interdigitated Ultramicroelectrode Arrays as Electrochemical Biosensor Transducers," *NNUN Report*, Cornell University, Ithaca, New York (Jan. 2002).

Min & Baeumner, "The Micro-total Analytical System for the Detection of Bacteria/Viruses," *J. Ind. Eng. Chem* 9(1):1-8 (2003).

Min et al., "RNA Biosensor Assays for the Rapid Detection of Viable *E. coli* in Drinking Water," Cornell University, Ithaca, New York (Feb. 2002).

Niwa et al., "Electrochemical Behavior of Reversible Redox Species at Interdigitated Array Electrodes with Different Geometries: Consideration of Redox Cycling and Collection Efficiency," *Anal. Chem.* 62:447-452 (1990).

Niwa et al., "Sinall-volume Voltammetric Detection of 4-Aminophenol with Interdigitated Array Electrodes and Its Application to Electronchemical Enzyme Immunoassay," *Anal. Chem.* 65:1559-15 63 (1993).

Park & Baeumner, "Development of Interdigitated Ultramicroelectrode Arrays for the Use in Nucleic Acid-based Biosensors," *Department of Agriculture and Biological Engineering*, Cornell University, Ithaca, New York (Sep. 14, 2000) (poster).

Parsons et al., "Multianalyte Assay System Developed for Drugs of Abuse," *Clin.Chem.* 39:1899-1903 (1993).

Pinnaduwage et al., "Stable Target-sensitive Immunoliposomes," *Biochem.* 31:2850-2855 (1992).

Plant et al., "Generic Liposome Reagent for Immunoassays," *Anal. Biochem.* 176:420-426 (1989).

Price et al.. "Development of a Simple and Rapid Universal RNA Biosensor," *NIH-BECON Conference* (May 31-Jun. 4, 2002).

Price et al., "Development of a Simple and Rapid Universal RNA Biosensor," *BIH-BECON Conference* (May 31-Jun. 4, 2002) (abstract).

Reeves at al., "Novel Optical Measurement Approach for the Quantitation of Liposome Immunomigration Assays," *Anal. Lett.* 28:2347-2352 (1995).

Roberts et al., "Investigation of Liposome-based Immunomigration Sensors for the Detection of Polychlorinated Biphenyls," *Anal. Chem.* 67:482-491 (1995).

Rosenzweig et al., "Laser-based Particle-counting Microimunoassay for the Analysis of Single Human Erythrocytes," *Anal. Chem.* 66:1771-1776 (1994).

Rule et al., "Characteristics of DNA-tagged Liposomes Allowing Their Use in Capillary-migration, Sandwich-hybridization Assays," *Anal. Biochem.* 244:260-269 (1997).

Rule et al., "Rapid Method for Visual Identification or Specific DNA Sequences Based on DNA-tagged Liposomes," *Clin. Chem.* 42(8):1206-1209 (1996).

Siebert et al., "Liposome Immunomigration Field Assay Device for Alachlor Determination," *Anal. Chim. Acta* 282:297-305 (1993).

Singh et al., "Application of Antibody and Fluorophore-derivatized Liposomes to Heterogeneous Immunoassays for D-Dimer," *Biotechnol. Prog.* 12:272-280 (1996).

Umeda et al., "Novel Liposome Immune Lysis Assay (LILA) for Determination of CRP Antigen Using Two Monoclonal Antibodies Recognizing Different Antigenic Determinants," *Acta Med. Okayama* 48(6):299-304 (1994).

Umeda et al., "Liposome Immune Lysis Assay (LILA). Application of Sandwich Method to Determine a Serum Protein Component With Antibody-bearing Liposomes," *J. Immunol. Meth.* 95:15-21 (1986).

Wiggans et al., "Microfluidic Mixing Elements: Designs, Modeling, and Testing," Department of Biological and Environmental Engineering, Cornell University, Ithaca, New York (May 2002).

Yap et al., "Liposome How Injection Immunoassay: Model Calculations of Competitive Immunoreactions Involving Univalent and Multivalent Ligands," *Anal. Chem.* 63:2007-11 (1991).

Zuk et al., "Enzyme Immunochromatography—A Quantitative Immunoassay Reqiring no Instrumentation," *Clin. Chem.* 31(7):1144-50 (1985).

European Search Report for European Patent Application No. 07123477.7 to Baeumner (May 8, 2008).

\* cited by examiner

| PROBE LENGTH | REFLECTOMETER READING |
|---|---|
| 17 nt | 11 |
| 20 nt | 38 |
| 25 nt | 27 |
| 30 nt | 5 |
| POS. CONTROL | 12 (LIPOSOMES OF AN OLD LOT) |

| C. parvum RNA [fmol/assay] | REFLECTOMETER READING |
|---|---|
| 0 | 6 |
| 50 | 10 |
| 100 | 8 |
| 250 | 10 |
| 500 | 19 |
| 1,000 | 14 |
| 2,500 | 19 |
| 5,000 | 20 |
| 10,000 | 18 |

UNIVERSAL BIOSENSOR AND METHODS OF USE

The present application is a continuation of U.S. patent application Ser. No. 10/449,369, filed May 30, 2003, and claims the benefit of U.S. Provisional Patent Application Ser. No. 60/385,146, filed May 31, 2002, which are hereby incorporated by reference in their entirety.

FIELD OF THE INVENTION

The present invention relates to methods for detecting or quantifying an analyte using a universal biosensor in which marker-loaded particles and/or capture membranes are adapted to any desired recognition element and analyte. Methods of using the device may employ marker-loaded particles, e.g., liposomes, and either electrochemical or optical detection of a target analyte in a test sample.

BACKGROUND OF THE INVENTION

Nucleic acid detection methods are potentially useful for detecting and measuring the presence of organisms, such as pathogens in food and water supplies. Southern, northern, dot blotting, reverse dot blotting, and electrophoresis are the traditional methods for isolating and visualizing specific sequences of nucleic acids. Each has advantages and disadvantages. For example, gel electrophoresis, often performed using ethidium bromide staining, is a relatively simple method for gaining fragment length information for DNA duplexes. This technique provides no information on nucleotide sequence of the fragments, however, and ethidium bromide is considered very toxic, although safer stains have been developed recently.

If, in addition to length information, there is a desire to determine the presence of specific nucleotide sequences, either Southern blotting, for DNA, or northern blotting, for RNA, may be chosen. These procedures first separate the nucleic acids on a gel and subsequently transfer them to a membrane filter where they are affixed either by baking or UV irradiation (a method that often takes several hours). The membrane is typically treated with a pre-hybridization solution, to reduce non-specific binding, before transfer to a solution of reporter probe. Hybridization then takes place between the probe and any sequences to which it is complementary. The initial hybridization is typically carried out under conditions of relatively low stringency, or selectivity, followed by washes of increasing stringency to eliminate non-specifically bound probe and improve the signal-to-noise ratio.

Originally, probes were often labeled with $^{32}P$ which was detected by exposure of the membrane to photographic film. Today, however, many researchers are making use of non-isotopic reporter probes. These blotting procedures require more time and effort than simple gel electrophoresis, particularly when low levels of nucleic acid are present. In particular, the entire process to detect a specific sequence in a mixture of nucleic acids often takes up to two days, and is very labor intensive and expensive.

There are a wide variety of DNA and RNA detection schemes in the literature, many of which are available as commercial kits. Nucleic acid detection schemes have seen the same trends in assay design as immunoassays, with efforts directed towards simpler, more rapid, and automatable detection schemes.

Liposomes are of interest as detectable labels in hybridization assays because of their potential for immediate signal amplification. Liposomes are spherical vesicles in which an aqueous volume is enclosed by a bilayer membrane composed of lipids and phospholipids (New, *Liposomes: A Practical Approach*, IRL Press, Oxford (1990)). Previous studies (Plant et al., *Anal. Biochem.*, 176:420-426 (1989); Durst et al., In: GBF Monograph Series, Schmid, Ed., VCH, Weinheim, FRG, vol. 14, pp. 181-190 (1990)) have demonstrated the advantages of liposome-encapsulated dye over enzymatically produced color in the enhancement of signals in competitive immunoassays. The capillary migration or lateral flow assays utilized in these experiments, avoid separation and washing steps and long incubation times and attain sensitivity and specificity comparable to enzyme-linked detection assays. Nevertheless, for each pathogenic organism, new liposomes and membranes have to be developed. This is a laborious and time-consuming process.

Accordingly, there remains a need for a simple, reliable universal biosensor utilizing generic components compatible with any analyte, such as environmental and food contaminants, including pathogenic organisms. The present invention is directed to overcoming these and other deficiencies in the art.

SUMMARY OF THE INVENTION

The present invention relates to a method for detecting or quantifying an analyte in a test sample. This method includes providing at least one test mixture comprising: a test sample, wherein the test sample potentially contains an analyte; a marker complex, wherein the marker complex comprises a particle, a marker, and a first member of a first coupling group; a first binding material, wherein the first binding material is selected to bind with a portion of the analyte and wherein the first binding material comprises a second member of the first coupling group; and a second binding material, wherein the second binding material is selected to bind with a portion of the analyte other than the portion of the analyte for which the first binding material is selected and wherein the second binding material comprises a first member of a second coupling group. The at least one test mixture is passed through a membrane having a second member of the second coupling group immobilized thereto. Reaction is permitted to occur between any analyte present and the first and second binding materials, between the first and second members of the first coupling group, and between the first and second members of the second coupling group. The presence or amount of the marker on the membrane is detected using a detection assembly and correlated with the presence or amount of the analyte in the test sample.

The present invention also relates to a method for detecting or quantifying an analyte in a test sample which involves providing at least one test mixture including a test sample, wherein the test sample potentially contains an analyte; a marker complex, wherein the marker complex comprises a particle, a marker, and a first member of a coupling group; and a first binding material, wherein the first binding material is selected to bind with a portion of the analyte and wherein the first binding material comprises a second member of the coupling group. The at least one test mixture is passed through a membrane having a second binding material immobilized thereto wherein the second binding material is selected to bind with a portion of the analyte other than the portion of the analyte for which the first binding material is selected. Reaction is permitted to occur between any analyte present and the first and second binding materials and between the first and second members of the coupling group. The presence or amount of the marker on the membrane is detected using a detection assembly and is correlated with the presence or amount, respectively, of the analyte in the test sample.

Another aspect of the present invention relates to a method for detecting or quantifying an analyte in a test sample including providing at least one test mixture including a test sample, wherein the test sample potentially contains an analyte; a marker conjugate, wherein the marker conjugate comprises a particle, a marker, and a first binding material, wherein the first binding material is selected to bind with a portion of the analyte; and a second binding material, wherein the second binding material is selected to bind with a portion of the analyte other than the portion of the analyte for which the first binding material is selected and wherein the second binding material comprises a first member of a coupling group. The at least one test mixture is passed through a membrane having a second member of the coupling group immobilized thereto. Reaction between any analyte present and the first and second binding materials and between the first and second members of the coupling group is permitted to occur. The presence or amount of the marker on the membrane is detected using a detection assembly and is correlated with the presence or amount, respectively, of the analyte in the test sample.

Yet another aspect of the present invention relates to a method of detecting or quantifying an analyte in a test sample. In this embodiment, the method involves providing a test mixture comprising: a test sample, wherein the test sample potentially contains an analyte; a first marker complex, wherein the first marker complex comprises a first particle, a first marker, and a first member of a first coupling group; a first binding material, wherein the first binding material is selected to bind with a portion of the analyte and wherein the first binding material comprises a second member of the first coupling group; a second marker complex, wherein the second marker complex comprises a second particle, a second marker, and a first member of a second coupling group; and a second binding material, wherein the second binding material is selected to bind with a portion of the analyte other than the portion of the analyte for which the first binding material is selected and wherein the second binding material comprises a second member of the second coupling group. Reaction between any analyte present and the first and second binding materials, between the first and second members of the first coupling group, and between the first and second members of the second coupling group is permitted to occur to form an aggregate. The aggregate is collected on a filtration device and the presence or amount of the marker on the filtration device is detected using a detection assembly. The presence or amount of the marker on the filtration device is correlated with the presence or amount, respectively, of the analyte in the test sample.

A further aspect of the present invention relates to a method for detecting or quantifying an analyte in a test sample. In this method, a membrane having a first binding material immobilized thereto is provided, wherein the first binding material is capable of binding to a portion of the analyte. The method also involves providing at least one test mixture comprising: a test sample, wherein the test sample potentially contains an analyte; a marker complex, wherein the marker complex comprises a particle, a marker, and a first member of a first coupling group; and an analyte analog, wherein the analyte analog comprises a second member of the first coupling group. Reaction between the first and second members of the first coupling group is permitted to occur. The test mixture is passed through the membrane under conditions effective to permit competition to occur between any analyte present and the analyte analog for the first binding material. The presence or amount of the marker on the membrane is detected using a detection assembly and is correlated with the presence or amount of the analyte in the test sample.

The present invention also relates to another method for detecting or quantifying an analyte in a test sample. This method involves providing at least one test mixture comprising: a test sample, wherein the test sample potentially contains an analyte; a marker complex, wherein the marker complex comprises a particle, a marker, and a first member of a coupling group; an analyte analog, wherein the analyte analog comprises a second member of the coupling group; and a binding material capable of binding to a portion of the analyte. Competition between any analyte present and the analyte analog for the bind material is permitted to occur. In addition, reaction between the first and second members of the coupling group is permitted to occur. The at least one test mixture is passed through a membrane. The presence or amount of the marker on the membrane is detected using a detection assembly and is correlated with the presence or amount, respectively, of the analyte in the test sample.

The universal biosensor of the methods of the present invention provides a simple, rapid, and reliable biosensor system utilizing generic components compatible with any target analyte. The marker-loaded particles and membrane of the biosensor of the present invention can be modified rapidly with specific binding materials. Thus, within a short period of time, the biosensor of the present invention can be made specific towards a desired target analyte. Thus, the universal biosensor of the present invention ameliorates the need to purchase individual biosensors or biosensor kits for each analyte to be detected or quantified. Rather, a single biosensor or biosensor kit can be purchased and the biosensor made specific for any desired analyte by the user. The kit may include universal marker complex(es) and/or universal membranes and may be used in the methods of the present invention. In addition, a library of suitably modified analyte-specific binding materials can be provided in a kit with the biosensor of the present application, such that rapid modification of the universal biosensor for a specific analyte can be made.

BRIEF DESCRIPTION OF THE DRAWINGS

FIG. 1A is a schematic showing a universal marker complex having one member of a coupling group bound to its surface. A binding material for the analyte modified to include the other member of the coupling group conjugates to the surface of the marker complex, to make the universal marker analyte-specific. FIG. 1B is a schematic showing a universal membrane having one member of a coupling group bound to its surface. A binding material for the analyte modified to include the other member of the coupling group conjugates to the surface of the membrane, to make the universal membrane analyte-specific.

DETAILED DESCRIPTION OF THE INVENTION

Figure 1A:
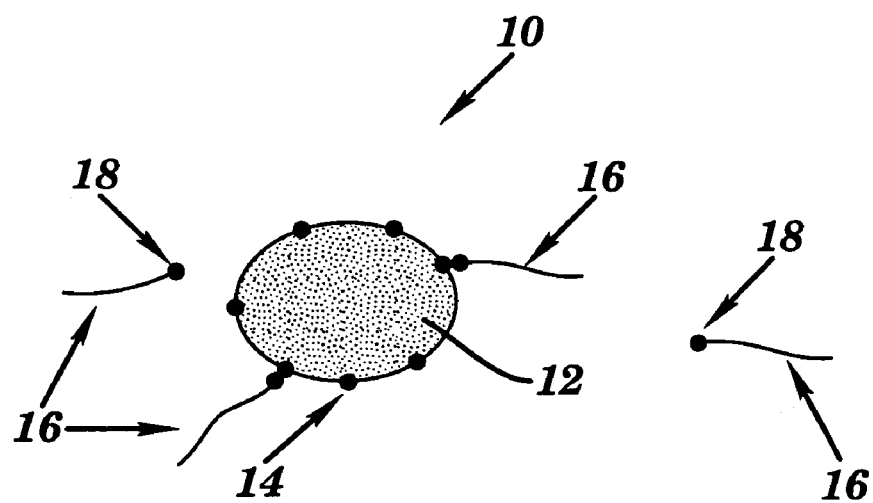
FIGS. 1A-B show a universal marker complex and universal membrane in accordance with the present invention.

In a first embodiment of the present invention, the method of the invention employs a first marker complex having a first member of a first coupling group immobilized thereto. A first binding material for a specific analyte of interest is then conjugated to the marker complex to form a first marker complex conjugate. The first binding material is modified to include a second member of the first coupling group. Thus, the first binding material for a specific analyte is quickly and simply conjugated to the universal marker complex through the first coupling group. The method may also employ a membrane having a first member of a second coupling group immobilized thereto. A second binding material for a specific analyte of interest is conjugated to a portion of the membrane. The second binding material is modified to include a second member of the second coupling group. Thus, the second binding material for the specific analyte is quickly and simply conjugated to the universal membrane through the second coupling group. The two binding materials bind to different portions of the analyte. An excess of both the first marker complex conjugate and the immobilized binding material are employed. Thus, to the extent that the analyte is present in the test sample, the marker complex becomes bound to the membrane via the analyte. Thus, the method of a first embodiment of the invention relies on the "sandwich" formed by the first binding material (conjugated to the marker complex), the analyte, and the second binding material (immobilized on the membrane). Alternatively, the universal marker complex may be used with an analyte-specific membrane (provided as specific for a single analyte prior to determination of an analyte of interest) or the universal membrane may be used with analyte-specific markers (provided as specific for a single analyte prior to determination of an analyte of interest).

In a second embodiment, the method of the invention employs a first marker complex having a first member of a first coupling group immobilized thereto. A first binding material for a specific analyte of interest is then conjugated to the first marker complex to form a first marker complex conjugate. The first binding material is modified to include a second member of the first coupling group. Thus, the first binding material for a specific analyte is quickly and simply conjugated to the first universal marker complex through the first coupling group. This method of the invention also employs a second marker complex having a first member of a second coupling group immobilized thereto. A second binding material for the specific analyte of interest is then conjugated to the second marker complex to form a second marker complex conjugate. The second binding material is modified to include a second member of the second coupling group. Thus, the second binding material for the specific analyte is quickly and simply conjugated to the second universal marker complex through the second coupling group. The two binding materials bind to different portions of the analyte. An excess of both marker conjugates are employed. Thus, to the extent that the analyte is present in the test sample, the first and second marker complexes become bound to each other via the first and second binding materials and the analyte. Thus, the method of a second embodiment of the invention relies on the "sandwich" formed by the first binding material (immobilized on the first marker complex), the second binding material (immobilized on the second marker complex), and the analyte. This "sandwich" forms aggregates of multiple marker complexes which can be filtered out of solution using a filter membrane.

In another embodiment of the present invention, the method of the invention employs a first marker complex having a first member of a first coupling group immobilized thereto. An analyte analog is then conjugated to the marker complex to form a first marker complex conjugate. The analyte analog is modified to include a second member of the first coupling group. Thus, the analyte analog for a specific analyte is quickly and simply conjugated to the universal marker complex through the first coupling group. In this method of the invention, the first marker complex and the analyte analog is mixed with a first binding material specific for the analyte and the analyte (either in solution or on a membrane), such that the analyte analog is conjugated to the first marker complex and the analyte and analyte analog compete for binding to the first binding material. The method may also employ a membrane having a receptor for the first marker complex immobilized thereto. An excess of both the first marker complex conjugate and the immobilized receptor are employed.

The invention encompasses both direct and indirect detection/measurement methods. In the former, the presence or amount of the marker bound in an immobilization or "capture" portion of the test device is detected. In this embodiment, the amount of marker bound in the capture portion is directly proportional to the amount of analyte in the test sample. The indirect detection embodiment involves detecting or measuring the marker which migrates beyond the capture portion, which is indirectly proportional to the amount of analyte in the test sample.

By "analyte" is meant the compound or composition to be measured or detected. It is capable of binding to the first and second binding materials. Suitable analytes include, but are not limited to, antigens (e.g., protein antigens), haptens, cells, and target nucleic acid molecules. A preferred analyte is a target nucleic acid molecule. A more preferred analyte is a target nucleic acid molecule found in an organism selected from the group consisting of bacteria, fungi, viruses, protozoa, parasites, animals (e.g., humans), and plants. Suitable organisms include, but are not limited to, *Cryptosporidium parvum, Escherichia coli, Bacillus anthracis*, Dengue virus, and Human immunodeficiency virus (HIV-1).

In one embodiment, the test device and methods of the present invention include immobilizing a second binding material specific for the analyte on the membrane. The second binding material is capable of binding to a portion of the analyte as the test mixture flows through the membrane through capillary action or passes through the membrane.

By "binding material" is meant a bioreceptor molecule such as an immunoglobulin or derivative or fragment thereof having an area on the surface or in a cavity which specifically binds to and is thereby defined as complementary with a particular spatial and polar organization of another molecule—in this case, the analyte. Suitable binding materials include antibodies, antigens, nucleic acid molecules, aptamers, cell receptors, biotin, streptavidin, and other suitable ligands. When the analyte is a target nucleic acid molecule, the first binding material can be a nucleic acid molecule (e.g., reporter probe, selected to hybridize with a portion of the target nucleic acid molecule) and the second binding material can be a nucleic acid molecule (e.g., capture probe, selected to hybridize with a separate portion of the target nucleic acid molecule), or other moiety, such as an antibody or other agent capable of binding to and interacting with the analyte.

Antibody binding materials can be monoclonal, polyclonal, or genetically engineered (e.g., single-chain antibodies, catalytic antibodies) and can be prepared by techniques that are well known in the art, such as immunization of a host and collection of sera, hybrid cell line technology, or by genetic engineering. The binding material may also be any naturally occurring or synthetic compound that specifically binds the analyte of interest.

In one embodiment of the present invention, an analyte analog is used. This embodiment is particularly suitable for a competitive binding assay. Thus, by "analyte analog" is meant an analog which includes the second member of a coupling group to react with or bind to the marker complex. When an analog is employed, however, it is necessary that the particular characteristics of the analyte necessary for recognition by the binding material in the competition reaction be present in the analyte analog conjugated with the marker complex.

The method of the invention employs marker complexes which include a particle, a marker, and one member of a coupling group. Suitable particles include liposomes (the marker may be encapsulated within the liposome, in the bilayer, or attached to the liposome membrane surface), latex beads, gold particles, silica particles, dendrimers, quantum dots, magnetic beads (e.g., antibody-tagged magnetic beads and nucleic acid probe-tagged magnetic beads), or any other particle suitable for derivatization.

In a preferred embodiment, the particle is a liposome encapsulating a marker. The first binding material and, if desired, second binding material may be conjugated to a liposome surface through first and second coupling groups, respectively. The first binding material and, if desired, second binding material must be bound to the liposome or other particle so as to present a portion of the first binding material (and second binding material) that may be recognized by the analyte.

In accordance with the present invention, the first and, if desired, second marker complexes may be provided as universal marker complexes, as shown in FIG. 1A. In particular, they each include one member of a coupling group. As shown in FIG. 1A, a marker complex 10 includes a particle 12 including one member 14 of a coupling group on its surface. The particle 12 includes a marker (not shown). Once a desired analyte is determined, the universal marker complexes are conjugated to a binding material specific for the desired analyte, thus making the marker complexes specific for the particular analyte. In particular, as shown in FIG. 1A, binding material specific for the analyte 16 is modified to include a second member 18 of the coupling group. The first and second members 14, 18 of the coupling group interact to immobilize the binding material 16 to the marker complex 10. The analyte-specific binding materials can be formed by obtaining or generating the binding material and modifying the binding material with a member of a coupling group. Alternatively, binding materials including a member of a coupling group may be selected from a previously produced library. Thus, the first binding material may be bound to the first marker complex through a first coupling group. If desired, the second binding material may be bound to the second marker complex through a second coupling group.

Figure 1B:
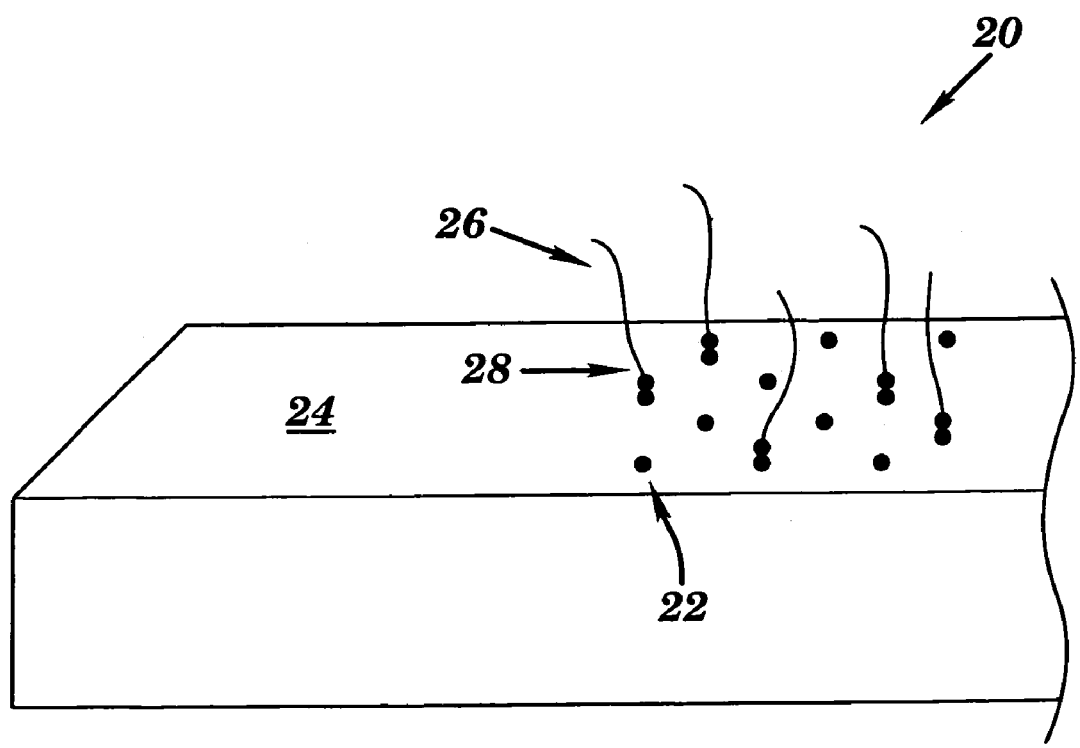

The methods and device of the present invention may also include a universal membrane, as shown in FIG. 1B. In particular, the universal membrane may be provided with one member of a coupling group immobilized thereto. As shown in FIG. 1B, the universal membrane 20 includes one member 22 of a coupling group on its surface 24. Once a desired analyte is determined, the universal membrane is conjugated to a binding material specific for the desired analyte, thus making the membrane specific for a particular analyte. In particular, as shown in FIG. 1B, binding material specific for the analyte 26 is modified to include a second member 28 of the coupling group. The first and second members 22, 28 of the coupling group interact to immobilize the binding material 26 to the membrane 20. As described above, the analyte-specific binding material can be formed by obtaining or generating the binding material and modifying the binding material with a member of a coupling group. Alternatively, a binding material including a member of a coupling group may be selected from a previously produced library. The binding material may be bound to the membrane through a second coupling group.

The method and device of the present includes one or both of the universal marker complexes and the universal membrane. Suitable analyte-specific marker conjugates and membranes for use with either the universal membranes or universal marker complexes, respectively, of the present invention, as well as methods of making them are described, for example, in U.S. Pat. No. 5,789,154 to Durst et al., U.S. Pat. No. 5,756,362 to Durst et al., U.S. Pat. No. 5,753,519 to Durst et al., U.S. Pat. No. 5,958,791 to Roberts et al., U.S. Pat. No. 6,086,748 to Durst et al., U.S. Pat. No. 6,248,956 to Durst et al., U.S. Pat. No. 6,159,745 to Roberts et al., U.S. Pat. No. 6,358,752 to Roberts et al., co-pending U.S. patent application Ser. No. 09/698,564, filed Oct. 27, 2000, and co-pending U.S. patent application Ser. No. 10/264,159, filed Oct. 2, 2002, which are hereby incorporated by reference in their entirety.

By "coupling group" is meant any group of two or more members each of which are capable of recognizing a particular spatial and polar organization of a molecule, e.g., an epitope or determinant site. Suitable coupling groups in accordance with the invention include, but are not limited to, antibody-antigen, receptor-ligand, biotin-streptavidin, sugar-lectins, and complementary oligonucleotides, such as complementary oligonucleotides made of RNA, DNA, or PNA (peptide nucleic acid). For example, an antibody, sufficiently different in structure from the analyte of interest, can be employed as a member of a coupling group for suitably derivatized binding material (i.e., derivatized with the specific antigen of the antibody). Illustrative members of the coupling groups include avidin, streptavidin, biotin, anti-biotin, anti-fluorescein, fluorescein, antidigoxin, digoxin, anti-dinitrophenyl (DNP), DNP, generic oligonucleotides (e.g., substantially dC and dG oligonucleotides) and the like. For example, in one preferred embodiment of the invention, biotin functions as one member of a coupling group for liposomes or a membrane derivatized with streptavidin or anti-biotin antibody.

Since the universal biosensor components (marker complexes and/or membrane) are provided with one member of a coupling group already attached, they are quickly and easily modified for a particular analyte. In particular, the binding material specific for the analyte of interest modified with the other member of the coupling group can be immobilized to the universal biosensor components by simple mixing and incubation. For example, when the coupling group is biotin-streptavidin, mixing and incubation of binding material(s) with the marker complex(es) and/or membrane results in conjugation through specific binding. Alternatively, when the coupling group comprises complementary oligonucleotides (e.g., an oligo dC generic oligonucleotide-oligo dG generic oligonucleotide), mixing the binding material(s) with the marker complex(es) and/or membrane results in direct coupling via DNA hybridization. Suitable conditions for conjugating the universal biosensor components with binding materials for a specific analyte will be determined by the coupling group used, and are described below. Application of members of coupling groups to the marker complex(es) and/or membrane of the present invention may be accomplished by well-known techniques, such as those described in the Examples, infra.

The first and second binding materials are selected to bind specifically to separate portions of the analyte. For example, when the analyte is a nucleic acid sequence, it is necessary to choose probes for separate portions of the target nucleic acid sequence. Techniques for designing such probes are well-known. Probes suitable for the practice of the present invention must be complementary to the target analyte sequence, i.e., capable of hybridizing to the target, and should be highly specific for the target analyte. The probes are preferably between 17 and 25 nucleotides long, to provide the requisite specificity while avoiding unduly long hybridization times and minimizing the potential for formation of secondary structures under the assay conditions. Thus, in this embodiment, the first binding material is reporter probe, which is selected to, and does, hybridize with a portion of target nucleic acid sequence. The second binding material, referred to herein as a capture probe for the nucleic acid detection/measurement embodiment, is selected to, and does, hybridize with a portion of target nucleic acid sequence other than that portion of the target with which reporter probe hybridizes. The capture probe may be immobilized in a capture portion of the membrane. In addition, the first and second binding materials (reporter and capture probes) should be capable of no or limited interaction with one another. Techniques for identifying probes and reaction conditions suitable for the practice of the invention are described in Sambrook et al., *Molecular Cloning: A Laboratory Manual*, Cold Spring Harbor Laboratory Press (1989), which is hereby incorporated by reference in its entirety. A software program known as "Lasergene", available from DNASTAR, may optionally be used.

Figure 2B:
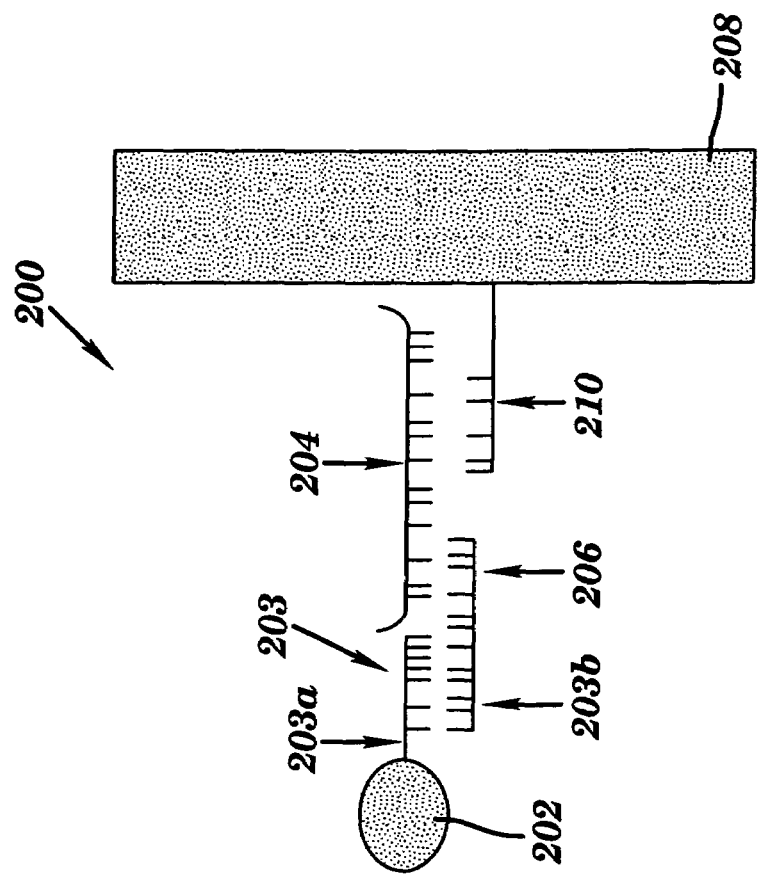
FIGS. 2A-B show a comparison of a specific nucleic acid biosensor of the prior art (FIG. 2A) and a universal nucleic acid biosensor in accordance with the present invention (FIG. 2B). The universal biosensor includes a universal marker complex having one member of a first nucleic acid coupling group immobilized thereto. A reporter probe having a second member of the first nucleic acid coupling group binds to the marker complex through the coupling group. The target then binds to the reporter probe and a target specific capture probe on a target-specific membrane.
Figure 2A:
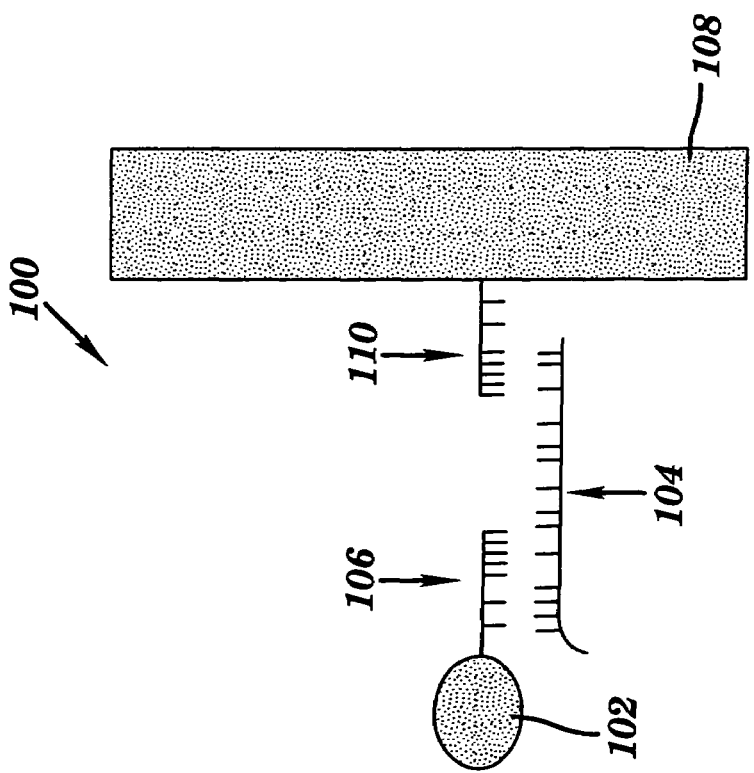

A schematic of a biosensor in accordance with the nucleic acid detection/measurement embodiment of the present invention, as compared to the prior art, is shown in FIG. 2. In particular, FIG. 2A shows a prior art target nucleic acid specific biosensor 100. The biosensor 100 includes a target specific marker 102 which binds to a portion of a target sequence 104. The target specific marker 102 includes a reporter probe 106 which binds to the target sequence 104. The biosensor 100 also includes a target specific capture membrane 108 which binds to a separate portion of the target sequence 104. The capture membrane 108 includes a capture probe 110 which binds to the target sequence 104. In contrast, a universal nucleic acid biosensor in accordance with the present invention is shown schematically in FIG. 2B. In FIG. 2B, like elements are numbered as in FIG. 2A, plus 100 (i.e., beginning with the number 2). Thus, biosensor 200 of the present invention includes a universal marker complex 202. The universal marker complex 202 includes a first member 203a of a coupling group 203 which binds to a second member 203b of coupling group 203 which is bound to reporter probe 206. The reporter probe 206 binds to the target sequence 204. The biosensor 200 also includes a target specific capture membrane 208 which binds to a separate portion of the target sequence 204. The capture membrane 208 includes a capture probe 210 which binds to the target sequence 204. Although, in FIG. 2B, the membrane 208 is a target-specific membrane, a universal membrane in accordance with the present invention could also be used.

In general, to design an assay, the target nucleic acid is extracted from a sample, and then amplified by one of a variety of known amplification techniques. Such amplification techniques include polymerase chain reaction, ligase chain reaction, and Nucleic Acid Sequence Based Amplification (NASBA). See Kievits et al., "NASBA Isothermal Enzymatic in vitro Nucleic Acid Amplification Optimized for the Diagnosis of HIV-1 Infection" *J. of Virological Methods* 35:273-286 (1991), which is hereby incorporated by reference in its entirety. NASBA, marketed by Organon-Teknika, is a preferred amplification technique when determining information regarding the presence or concentration of viable organisms in a sample. However, the target nucleic acid need not be amplified in accordance with the present invention.

As discussed further below, the test sample known to or suspected of containing the analyte can be combined with the first marker complex (and the second marker complex, if desired) and first and second binding materials to form a mixture, which may be a solution, suspension, dispersion, or other mixture. The mixture is then applied to the membrane. Alternatively, when the second binding material is to be immobilized on the membrane, the membrane may be contacted with the second binding material independently from forming the mixture of the test sample, the universal marker complex(es), and the first binding material. In yet another embodiment, the test sample, the universal marker complex(es), and the binding material(s) may be applied separately to the membrane, for example, by spotting each onto the absorbent material in the same or separate locations.

In accordance with one embodiment of the present invention, the membrane may be an "absorbent material." This embodiment of the present invention is particularly suitable for a "lateral flow" assay. By "absorbent material" is meant a porous material having a pore size of from 0.05 μm to 50 μm, preferably from 0.45 μm to 5 μm, which is susceptible to traversal by an aqueous medium in response to capillary force. Such materials may be natural polymeric materials, particularly cellulosic materials, such as fiber-containing papers, e.g., filter paper, chromatographic paper, etc.; synthetic or modified naturally occurring polymers, such as nitrocellulose, cellulose acetate, poly(vinyl chloride), polyacrylamide, cross linked dextran, agarose, polyacrylate, nylon, activated nylon, polysulfone base modified, etc.; either used by themselves or in conjunction with a support, as described below. Polysulfones and nitrocellulose are preferred absorbent materials for the absorbent pad(s) comprising contact and capture portions of the test device, as described below.

The absorbent materials may be polyfunctional or be capable of being polyfunctionalized to permit immobilization of the second binding material through the second coupling group, as well as to permit bonding of other compounds which form a part of the signal producing system.

The absorbent materials employed in the test device and method of this embodiment of the invention may be a cellulose ester with nitrocellulose giving exceptionally good results. It is to be understood that the term "nitrocellulose" refers to nitric acid esters of cellulose, which may be nitrocellulose alone, or a mixed ester of nitric acid and other acids, and in particular, aliphatic carboxylic acids having from one to seven carbon atoms, with acetic acid being preferred. Such materials, which are formed from cellulose esterified with nitric acid alone, or a mixture of nitric acid and another acid such as acetic acid, are often referred to as nitrocellulose paper.

Although nitrocellulose is a preferred material for this method and test device of the present invention, it is to be understood that other materials, having a surface area sufficient for supporting the agents to be immobilized thereon in a concentration as hereinbelow described, and, if desired, a pore size suitable for accumulating aggregates formed from the marker complex, binding material specific for the analyte, and analyte analog may also be employed for producing such test devices.

Moreover, in the lateral flow embodiment of the present invention, the absorbent material preferably includes a contact portion and a capture portion. Suitable membranes/test devices are described, for example, in U.S. Pat. No. 5,789,154 to Durst et al., U.S. Pat. No. 5,756,362 to Durst et al., U.S. Pat. No. 5,753,519 to Durst et al., U.S. Pat. No. 5,958,791 to Roberts et al., U.S. Pat. No. 6,086,748 to Durst et al., U.S. Pat. No. 6,248,956 to Durst et al., U.S. Pat. No. 6,159,745 to Roberts et al., U.S. Pat. No. 6,358,752 to Roberts et al., and co-pending U.S. patent application Ser. No. 10/264,159, filed Oct. 2, 2002, which are hereby incorporated by reference in their entirety. In particular, the membrane is an absorbent material which includes a contact portion where the test sample, universal marker complexes, and first (and second) binding material containing solution(s) or mixture(s) is applied. The absorbent material further includes a capture portion, to which the second binding material is non-diffusively bound through the second coupling group.

In a first embodiment, as the test sample mixture migrates from the contact portion into the capture portion or in solution prior to application to the membrane, the first marker complex having a first member of a first coupling group bound thereto binds with the first binding material having a second member of the first coupling group bound thereto through the coupling group, and any analyte present in the test sample binds with the first binding material. This transversal of the membrane can be upward, downward, horizontal, or combinations thereof. Because the first binding material is selected to bind with only a portion of the analyte, the analyte also remains available for binding with the second binding material, as the test components migrate into capture portion. The second binding material may be present in the test sample mixture, such that it binds with any analyte present in the test sample, and then binds with the membrane in the capture portion through the second coupling group. Alternatively, the membrane may be separately contacted with the second binding material, such that the second binding material is bound to the membrane through the second coupling group, and then marker complex and first binding material migrates into the capture portion and binds to the second binding material through any analyte present in the test sample.

In accordance with the above-described embodiments of the present invention, a quantity of marker-loaded particles which is proportional to the concentration of the analyte in the test sample becomes bound in the capture portion of the test device. Thus, the signal-producing system provides a detectable signal at the capture portion only when the target analyte is bound to the second binding material in the capture portion, so that the presence of the target analyte may be determined by detecting the signal at the capture portion.

In constructing the test devices in accordance with the lateral flow embodiment of the invention, the position of the contact and capture portion (or portions, where a plurality of analytes are being determined), should be governed by the basic principle involved in this embodiment of the present invention. For example, whether the test sample, universal marker complex, and first binding material are applied to the same or separate locations in the contact portion of the test device, one desires to provide sufficient opportunity for binding to occur between the first binding material, the marker complex, and any analyte present in the test sample so that the concentration of the conjugate bound in the capture portion accurately reflects the concentration of the analyte in the test sample. Generally speaking, if nitrocellulose having a pore size of 8 μm is employed for the first or first and second membranes, the distance between the contact portion and the capture portion should range from about 5 mm to about 20 mm. If several capture portions are used for multi-analyte determinations, the capture portions can be grouped close together or apart but must not be so close as to compromise resolution of the signals. Consequently, such capture portions usually should be spaced not less than 0.5 mm apart, preferably at least 1 mm apart. In addition, the capture and contact portions should be separated sufficiently to avoid premature or unwanted contamination of the capture portion through human error in manipulating the device. When there are multiple capture portions positioned on the absorbent material (as described below for multi-analyte testing) the individual capture zones may be close to one another and may, in certain cases, even overlap.

As described herein, one or more absorbent materials may be used. In one embodiment, that portion of the absorbent material(s) comprising and between the contact and capture portions is made of a non-liposome lysing material. The material on which the second binding material is immobilized must be capable of supporting the immobilization, and in accordance with this embodiment of the present invention, the material(s) must allow liquid migration (lateral flow).

Absorbent materials having high surface areas (such as nitrocellulose) are particularly preferred for some applications in that the second binding material, if desired, may be supported on such materials in high concentrations. It is to be understood, however, that the concentration of second binding material which is actually used is dependent in part on the binding affinity of the second binding material. Accordingly, the scope of the invention is not limited to a particular concentration of binding material on the absorbent material.

The test device and method of the invention may comprise only one pad, as for example, when the sample volume is small. In such a case, it is necessary that the absorbent material have sufficient area beyond the capture portion to absorb sufficient volume of test reagents to permit completion of the reactions or hybridizations on which the assay is based, as discussed more fully below, and, in the case of the indirect measurement embodiment disclosed herein provide space for a sufficient separation between the capture portion and the portion at which the marker is measured or detected.

Two or three absorbent pads, laid end-to-end may also be used. In the two pad embodiment, the first pad includes both the contact portion and the capture portion, which preferably begins at or beyond about half-way along the absorbent material, to allow sufficient space on the pad in front of the capture zone for reaction or hybridization of the analyte with the first binding material and the first marker complex. A second pad may be employed as a wicking pad, as discussed more fully below, to pull excess reagents out of the first absorbent pad. If three pads are employed, the capture portion is preferably located on the center pad, most preferably at or near the center of the pad. In this embodiment, the wicking pad is the third pad, but an additional pad or pads could be used as wicking pads beyond a third pad.

A separate absorbent pad may be employed as a wicking pad, regardless of how many other absorbent pads are employed. The wicking pad serves to pull the liquid sample along the test strip formed by absorbent pads. The wicking material and pad length are preferably matched to the other components of the device and the particular test components employed in order to provide sufficient fluid flow contact along the test strip. A preferred wicking material is Whatman filter paper.

If more than one absorbent pad is employed, the pads are laid end to end, and preferably overlap slightly to ensure good fluid flow contact. The pads are preferably laminated together where they contact one another, for example, with plastic and glue. Alternatively, contact is maintained between the overlapped portions by virtue of pressure applied to the test strip by a cassette in which the test strip is held. Suitable cassettes are described, for example, in U.S. Pat. No. 6,358,752, which is hereby incorporated by reference in its entirety.

The test device can be modified to include an additional channel or channels to provide linear interpolation and verification of response. For example, a three-channel device can be constructed for the simultaneous measurement of the analyte in a test sample and high- and low-level control compositions. It should also be recognized that single channel devices are within the scope of the present invention.

Moreover, in the lateral flow embodiment of the present invention, the migration of the test sample and marker complex-binding material conjugate is preferably assisted by introducing a wicking reagent, preferably a buffer solution, onto the strip to carry the test components along the strip. Alternatively, if the sample volume is sufficiently large, it is not necessary to employ a separate buffer solution.

In another embodiment of the present invention, the membrane is a filter membrane. This embodiment of the invention is particularly suitable for a "flow through" assay. By "filter membrane" is meant a porous material having a pore size of from about 0.1 µm to about 100 µm, preferably from about 2 µm to about 30 µm, which allows an aqueous medium to flow therethrough. The pore size has an important impact on the performance of the device. The pore size has to be larger than the mean diameter of marker complexes (i.e., signal producing elements used). Also, the pores should not be too large so that a good volume to surface ratio can be obtained. Additionally, the membrane material must allow the retaining of the first marker complex conjugate-analyte-second marker complex conjugate aggregate (or other signal producing elements) when desired and the flow through of signal producing elements (e.g., marker complex which is not bound to analyte) when desired. Manufacturers of membranes include Schleicher & Schuell, Pall/Gelman, Sartorius, Whatman, and Millipore. Preferably, the filter membrane allows components of the test mixture not bound to the first binding material and second binding material, and thus the first and second marker complexes, to flow through.

Suitable filter membranes for the device and methods of the invention include nitrocellulose membranes, nitrocellulose mixed esters, mylar membranes, polysulfonyl based membranes, plain filter paper, glass fiber membranes, and membranes of any plastic material with defined pore size, such as polycarbonate filters, porous gold, and porous magnetic material. The filter membranes can be of a variety of shapes, including rectangular, circular, oval, trigonal, or the like.

In accordance with the "flow-through" embodiment of the present invention, a test mixture including the test sample, marker complex, and the first binding material flows through and out of a filter membrane (rather than lateral flow through an absorbent material). If the second binding material is bound to the membrane through the second coupling group, it binds to any analyte present in the test mixture, which is also bound to marker complex through the first binding material. The remaining components of the mixture, including any marker complex-binding material conjugate which is not bound to analyte, pass through and out of the filter membrane. Alternatively, a test solution including the test sample, first marker complex, first binding material, second marker complex, and second binding material flows through a filter membrane. If analyte is present, it binds to both the first binding material (which also binds to the first marker complex) and the second binding material (which also binds to the second marker complex) to form marker complex aggregates. The aggregates, which are too large to pass through the filter membrane, are collected on the membrane, while the remaining components of the solution, including any marker conjugate which is not bound to analyte, pass through and out of the filtration membrane.

In accordance with this embodiment, the membrane may be incorporated in a filtration-detection device for optical or electrochemical detection. Suitable filtration-detection devices, methods of making them, and methods of use are described in co-pending U.S. patent application Ser. No. 09/698,564, filed Oct. 27, 2000, which is hereby incorporated by reference in its entirety.

Application of members of coupling groups and members of the signal producing system (e.g., liposome lysing agents and marker accumulating agents) to the membrane of the present invention (absorbent material or filter membrane) may be accomplished by well-known techniques, for example, by spraying or spotting a solution of those materials onto the membrane.

The amount of coupling group member which is bound to the membrane will vary depending upon the amount required to bind the second binding material and, subsequently, marker complex-analyte conjugate to enable an effective assay. Generally, the amount of coupling group member immobilized on the membrane will be at least about 20 µmol/cm$^2$. However, as described above, the invention is not limited to a particular concentration of coupling group member on the absorbent material.

The coupling group member and members of the signal producing system (such as liposome lysing agents and marker accumulating agents) can be bound to the membrane by covalent bonding, physisorption, chemisorption, or any other means. For example, the material to be bound can be applied directly to the membrane, and then bonded thereto via ultraviolet radiation. Alternatively, materials can be adsorbed onto the membrane, as long as the binding of the second binding material to the membrane is non-diffusive. This will involve contacting the absorbent material with a solution containing the material to be bound to the membrane and allowing the membrane to dry. In general, this procedure will be useful only where the membrane is relatively hydrophobic or has a high surface charge, and subsequent treatment with proteins, detergents, polysaccharides, or other materials capable of blocking nonspecific binding sites will be required.

Before or after application of the coupling group member, the second binding material, and/or receptor signal-producing components (e.g., the liposome lysing agent and marker accumulating agent) to the appropriate portion(s) on the membrane, the residual nonspecific binding capacity of the membrane(s) can be, and preferably is, saturated or blocked with blocking agents which typically include a combination of three compounds: proteins, synthetic polymers, and surfactants, and which do not specifically bind the materials to be employed in the assay. Blocking is generally carried out after the coupling group member is applied to the membrane, but it may be possible to block the membrane before the coupling group member is applied depending on the method of application, the particular blocking agent, and membrane employed. Thus, for example, the residual binding capacity of the membrane may be blocked so as to prevent nonspecific binding by the use of bovine serum albumin, as described in Towbin et al., *Proc. Nat'l. Acad. Sci.* 76:4350 (1979), which is hereby incorporated by reference in its entirety. The techniques for preventing non-specific binding are generally known in the art, and such techniques are also generally applicable to preventing nonspecific binding in the assay of the present invention. Examples of particularly suitable techniques for blocking with polyvinylpyrrolidone and polyvinylalcohol are described, for example, in Bartles, et al. *Anal. Biochem.* 140:784 (1984), and in British Patent Specification GB 2204398 A, respectively, which are hereby incorporated by reference in their entirety. Alternatively, one or more blocking agents can be incorporated into the buffer solution used to wash or carry test components into or along the membrane(s).

The blocking agents block nonspecific binding sites on the membrane. The blocking agents are selected from the group consisting of proteinaceous blocking reagents capable of inhibiting binding of molecules having a molecular weight of greater than about 1000 with said membrane and polymer blocking reagents capable of inhibiting binding of molecules having a molecular weight of less than about 1000 with said membrane. The proteinaceous blocking reagent may be selected from the group consisting of gelatin, non-fat dry milk, bovine serum albumin, keyhold limpet hemocyanin, and casein. The polymer blocking reagent may be selected from the group consisting of polyvinylpyrrolidone and polyvinylalcohol, and the surfactant may be selected from the group consisting of polyoxyethylene ethers, polyoxyethylenesorbitan monolaurate, t-octylphenoxypolyethoxyethanol, sodium dodecylsulfate, octylglucopyranoside, and sodium dioxycholate.

In conjunction with a blocking reagent or reagents, a surfactant may be applied to the membrane to facilitate migration of liposome conjugate(s) without lysis of the liposomes. Suitable surfactants include Brij™ (polyoxyethylene ether), Tween 20™ (polyoxyethylenesorbitan monolaurate), Triton X-100™ (t-octylphenoxypolyethoxyethanol), sodium dodecylsulfate, n-octyl-β-D-glucopyranoside, Span 20™, Nonindet P-40, Chapso™, Turgitol™ and sodium dioxycholate. The concentration of the surfactant(s) employed in a blocking solution will depend, in part, upon the particle, e.g., liposome, composition. In general, surfactants may be incorporated in a concentration of from about 0 to about 0.01 volume percent of the blocking solution, preferably from about 0.001 to about 0.005 volume percent of the blocking solution. It is important that the concentration of surfactant applied to the membrane be controlled, as premature lysis of the liposomes may occur if the surfactant concentration is too high. Preferred surfactants include polyoxyethylene ethers, polyoxyethylenesorbitan monolaurate, t-octylphenoxypolyethoxyethanol, sodium dodecylsulfate, octylglucopyranoside, and sodium dioxycholate.

Blocking agents are applied in a buffer solution to the membrane. Suitable buffers solutions include Tris(hydroxymethyl)aminomethane/HCl (Tris/HCl), Tris/citrate, Tris/maleate, Tris/glycine, phosphate buffer, HEPES, and other biological buffers in the correct pH range.

In some cases, a pre-wash of the membrane is recommended (e.g. in the case of Sartorius membranes). This pre-wash can be done, for example in a 0.02 M Tris-HCL buffer containing 150 mM NaCl, pH 7.0 containing 5% methanol.

The membrane(s) can be a single structure such as a sheet cut into strips. The membrane(s) can be mounted on a support material, described more fully below. On the other hand, the membrane(s) may provide its own support. In one embodiment of the invention, the membrane is a strip of particulate material bound to a support or solid surface such as found, for example, in thin-layer chromatography. The membrane can be a sheet having lanes thereon, or be a uniform sheet capable of division into separate lanes by physical removal of the membrane from the support to induce lane formation, wherein a separate assay can be performed in each lane, as shown in U.S. Pat. No. 5,958,791, which is hereby incorporated by reference in its entirety. The membrane(s) can be a variety of shapes, including rectangular, circular, oval, trigonal, or the like. In one embodiment, there is at least one direction of traversal of a test mixture by capillary migration. Other directions of traversal may occur such as in an oval or circular piece contacted in the center with the test mixture. However, for the lateral flow embodiment of the present invention, the main consideration is that there be one direction of flow from the contact portion through the capture portion. In this discussion, strips of membrane are described by way of illustration and not limitation.

The support for the membrane where a support is desired or necessary will normally be hydrophobic, water insoluble, non-porous, and rigid, and usually will be of the same length and width as the absorbent strip but may be larger or smaller. A wide variety of organic and inorganic materials, both natural and synthetic, and combinations thereof, may be employed, provided only that the support does not interfere with the production of signal from the marker. Illustrative polymers include polyethylene, polypropylene, poly(4-methylbutene), polystyrene, polymethacrylate, poly(ethylene terephthalate), nylon, poly(vinyl chloride) poly(vinyl butyrate), glass, ceramics, metals, and the like.

The size of the piece(s) of membrane is dependent on several considerations. The following discussion is primarily focused on strips of membrane for use in the lateral flow embodiment, for purpose of illustration and not limitation. As mentioned above, other shapes such as circular, oval, trigonal, and the like, fall equally within the scope of this invention. The dimensions thereof and other parameters can be determined by those skilled in the art with reference to the disclosure herein.

When capillary flow is predominantly upward, the length and thickness of the strip control the amount of mixture that can pass through the measurement portion. If the transfer of a large volume of test mixture is desired, the fluid capacity of the strip beyond the capture portion must be sufficient to accommodate the desired volume. Alternatively, an additional absorbing material, absorbing pad, or sponge, referred to herein as a wicking pad, may be used to contact the end of the strip beyond the capture portion. A wicking pad may be used in this manner in situations when it is desirable to pull a larger volume of the test mixture across the test device.

To permit conservation of reagents and provide for samples of limited size, the dimensions of the membrane are preferably relatively small. Generally, the width of the strip will be from 1 mm to 20 mm and the length of the strip will be from 1 mm to 100 mm.

As is described in detail below, the test device in accordance with the invention may be modified for simultaneous multiple analyte detection or determination. The length of the strip will depend on the concentration of the analyte and practical considerations such as ease of handling and the number of capture portions on the strip and will be about 4 cm to 20 cm, usually about 5 cm to 15 cm, preferably about 6 to 13 cm, but may be of any practical length. The structure of the strip can be varied widely and includes fine, medium fine, medium, medium coarse, and coarse. Selection of the porosity of the material may be based on the rate of binding of the components for a given assay.

The marker complex(es), binding material(s), and analyte can be introduced into the device and method in a variety of ways, including single or multiple test mixtures (introduced sequentially or substantially simultaneously) with reactions between components occurring in solution or on the membrane. In one embodiment, first marker complex, first binding material, and second binding material are preferably combined with the test sample and may be incubated for a period of time to allow the first binding material to bind to the first marker complex via the first coupling group and reaction or hybridization to occur between any analyte present in the sample and the first binding material on the conjugate. Alternatively, first marker complex, second marker complex, first binding material, and second binding material are combined with the test sample and may be incubated for a period of time to allow the first binding material to bind to the first marker complex via the first coupling group, the second binding material to bind to the second marker complex via the second coupling group, and reaction or hybridization to occur between any analyte present in the sample and the first and second binding materials on the conjugates. Where the analyte is a nucleic acid molecule, the mixture is typically incubated at from about 15° C. to about 50° C., preferably, from about 30° C. to 50° C., more preferably from about 40° C. to 44° C., for about 3 to 30 minutes.

In another embodiment, the first marker complex, the first binding material (a second marker complex, a second binding material, if desired), and the test sample are introduced onto the absorbent material in the contact portion, at the same location or at a separate locations. Another alternative involves introducing the second binding material just before application of a mixture including the first marker complex, the first binding material, and the analyte. The second binding material may be introduced at the contact portion or directly onto the capture portion of the membrane.

The universal liposomes and membranes of the present invention may also be used in a competitive binding assay format. In particular, membranes in accordance with this aspect of the present invention may comprise a region for accumulation of aggregates formed from marker complex, analyte analog, and a binding material for the analyte, as described in more detail, below. For test devices comprising an electrochemical measurement portion, this region for accumulation is positioned away from the liposome lysing agent, and either between the liposome lysing agent and the contact portion, or in the contact portion. For the other test devices in accordance with the invention, this region for accumulation is positioned away from the capture portion, and either between the capture portion and the contact portion, or in the contact portion.

The mixture containing the marker complex including one member of a coupling group, analyte analog modified with the other member of the coupling group, a binding material, and the analyte (if present) is then incubated for a time sufficient to permit the analyte analog to bind to the marker complex and the analyte analog and the analyte to compete with one another for binding with the binding material. The incubation time will vary with the particular assay, however, in most cases, from about less than 1 minute to about 30 minutes will be sufficient to allow the competition reaction to reach or approach completion. Incubation times of from about 1 minute to about 30 minutes are easily achieved with the method of the invention, and are preferred, as one of the significant advantages of the present invention is the speed with which testing for analytes can be carried out. As one skilled in the art will appreciate, it is important that the competition reaction be permitted to approach completion, to avoid inaccurate results. However, it may be necessary to control the reaction time in some cases, because liposome-entrapping flocculants may form if the incubation period is too long.

Following incubation of the solution, the membrane is contacted with the test mixture. Wetting of the membrane by capillary action is allowed to continue at least until the capture portion is wet, (and preferably, until the solvent front reaches the end of the membrane). The test mixture continues to traverse the membrane into and through the capture portion, where the marker complex-analyte analog-binding material conjugate is trapped and accumulated by a specific receptor for the marker complex bound thereto. By "receptor" is meant any compound or composition capable of recognizing a particular spatial and polar organization of a molecule, e.g., an epitope or determinant site. Suitable receptors in accordance with the invention include those capable of binding directly with the surface of the liposomes, or with a molecule bound on adhered to the surface of the liposomes. For example, an antibody specific for a liposome tag, sufficiently different in structure from the analyte of interest can be employed as a receptor for suitably derivatized liposomes. Illustrative receptors include naturally occurring receptors, e.g., egg white avidin, streptavidin, thyroxine binding globulin, antibodies, Fab fragments, lectins, nucleic acids, protein A, protein G, and the like. For example, avidin or more preferably, anti-biotin antibody, may function as receptors for liposomes derivatized with biotin. Alternatively, egg white avidin can be employed as the receptor, as it will bind directly to the liposome surface.

In another embodiment of the competitive binding embodiment of the method of the invention, the binding material specific for the analyte may be provided immobilized on the membrane, rather than in the test mixture. In this embodiment, competition between the analyte analog and the analyte, if present, occurs on the membrane. Alternatively, two or more mixtures including the marker complex, analyte analog, and/or binding material may be applied at the same or different locations on the membrane, such that reaction between the members of the coupling group immobilized to the marker complex and analyte analog and competition between the analyte analog and the analyte, if present, occurs on the membrane.

In yet another embodiment of the competitive binding embodiment of the method of the invention, analyte analog and a marker complex are combined in an aqueous medium with a sample suspected of containing the analyte and a binding material specific for the analyte, to provide an aqueous test mixture. The marker complex has multiple members of a coupling group immobilized thereto, such that multiple analyte analog molecules will bind thereto. Therefore, the marker complex-analyte analog conjugate has multiple binding sites for the binding material. In the absence of the analyte, binding material will react exclusively with the conjugate, resulting in the formation of relatively large aggregates, each of which may include multiple marker complexes. During migration of the test mixture across the test device, the large aggregates formed during the incubation will tend to be retained in the interstices of the nitrocellulose matrix and will form an "aggregation zone" on the absorbent material, usually at or near the meniscus of the test mixture when the device is inserted into the test mixture. By occupying binding sites on the binding material, the analyte inhibits conjugate aggregation. Thus, the greater the concentration of analyte in the test sample, fewer aggregates will form and those that do form will be relatively limited in size. Smaller particles, including unaggregated marker complex-analyte analog conjugate, will not be retained at the "aggregation zone" and will continue to migrate until bound in the capture zone. The conjugates that do not aggregate will be proportional to the amount of analyte in the mixture, and will bind to the capture portion. Thus, the present invention provides for an immunoseparation of aggregated conjugate from unaggregated conjugate. This is accomplished as a result of the inability of aggregated conjugate to proceed beyond a certain position on the absorbent material.

The test sample may be derived from a wide variety of sources, such as physiologic fluids, illustrated by saliva, sweat, serum, plasma, urine, tear fluid, spinal fluid, etc., chemical processing streams, food, waste water, natural waters, air, soil extracts, etc. In carrying out the method of the invention, the sample suspected of containing the analyte may be combined with the universal liposomes and first binding material (and other desired components) in an electrolytic aqueous medium to form an aqueous test mixture or solution. Various addenda may be added to adjust the properties of the test mixture, or of a carrier solution used as a wicking reagent, depending upon the properties of the other components of the device, as well as on those of the marker complexes, conjugates, or the analyte itself. Examples of solution addenda which may be incorporated into test, control, or carrier solutions or mixtures in accordance with the invention include buffers, for example, pH and ionic strength, sample or analyte solubilizing agents, such as, for example, nonpolar solvents, and high molecular weight polymers such as Ficoll®, a nonionic synthetic polymer of sucrose, available from Pharmacia, and dextran.

The order of addition of the test sample (suspected of containing the analyte), the marker complex(es), the analyte analog, marker conjugate, the first binding material, and/or the second binding material to one another is not critical. For the competitive binding embodiment, it is preferred to allow the binding material and test sample to interact briefly before the addition of the first marker complex and analyte analog to compensate for the competitive advantage enjoyed by the first marker complex-analyte analog conjugate with its multiple binding material binding sites.

The method of addition of the test sample, the marker complex(es), the analyte analog, marker conjugate, the first binding material, and/or the second binding material (combined in a test mixture) to the membrane is also not critical. For example, in the lateral flow embodiment, the contact portion of the membrane may be contacted with test mixture(s), for example, by immersion of the contact portion into the test mixture(s). Alternatively, the test mixture(s) may be contacted with the absorbent material by spotting the test mixture(s) (preferably following incubation to permit reaction or hybridization) onto the membrane in the contact portion. Alternatively, the test sample, the marker complex(es), the analyte analog, marker conjugate, the first binding material, and/or the second binding material, preferably in buffer solution, may be applied separately to the contact portion, either in the same location or in separate locations, as long as the components will come in contact with one another as they migrate across or through the membrane(s).

In the lateral flow embodiment of the present invention, wetting of the first membrane and the second membrane, if present, by capillary action is allowed to continue until a sufficient volume of test mixture and/or buffer solution has passed through the capture portion to ensure that any analyte present in the test has reached the capture portion. If detection alone is desired, less care must be taken to ensure that all analyte has reached the capture portion. It is possible to "calibrate" run times and buffer volumes using pre-runs employing electrochemical detection and measurement as described in U.S. Pat. No. 6,358,752, or colorimetric detection, as described, for example, in Rule et al., *Clin. Chem.* 42:1206-1209 (1996), which are hereby incorporated by reference in their entirety.

For the most part, relatively short times are involved for the test mixture to traverse the membrane in the lateral flow embodiment of the present invention. Usually, traversal of the test mixture over the strip will take at least 30 seconds and not more than 45 minutes to 1 hour, more usually from about 1 minute to about 10 minutes. In accordance with the method of the invention, the signal is rapidly, even immediately, detectable.

As described above, in the lateral flow embodiment of the present invention, movement of the test components along the membrane(s) is due to capillary action. This capillary movement along the membrane causes the test mixture to be carried to and through the capture portion, where measurement of the marker-loaded liposomes takes place.

In the "flow-through" embodiment of the present invention, a test mixture of the test sample and the aggregates (formed by the first and second binding material, each having bound thereto a marker complex including a particle and a marker, and analyte) is prepared using the first and second marker complexes. The solution is passed through the filter membrane such that aggregates are collected on the filter membrane and the filter membrane is washed. Alternatively, a test mixture of the test sample, first marker complex, and first binding material is passed through the filter membrane such that conjugates of the first marker complex, first binding material, and analyte are captured on the filter membrane through second binding material bound to the filter membrane. The second binding material may be provided in the test mixture or previously bound to the filter membrane. Detection of immobilized conjugate or collected aggregate is then performed, as described below.

As hereinabove indicated, the signal producing system includes a marker complex which includes a particle, a marker, and one member of a coupling group, e.g., a marker within the interior of derivatized liposomes. Suitable markers include fluorescent dyes, visible dyes, bio- and chemiluminescent materials, quantum dots, enzymes, enzymatic substrates, radioactive materials, and electroactive markers. When using liposomes as the particle, visible dyes and radioactive materials can be measured without lysis of the liposomes. Lysis of the liposomes in the device and methods of the present invention may be accomplished by applying a liposome lysing agent to the membrane, for example, in the capture zone. Suitable liposome lysing materials include surfactants such as octylglucopyranoside, sodium dioxycholate, sodium dodecylsulfate, saponin, polyoxyethylenesorbitan monolaurate sold by Sigma under the trademark Tween-20, and a non-ionic surfactant sold by Sigma under the trademark Triton X-100, which is t-octylphenoxypolyethoxyethanol. Octylglucopyranoside is a preferred lysing agent for many assays, because it lyses liposomes rapidly and does not appear to interfere with signal measurement. Alternatively, complement lysis of liposomes may be employed, or the liposomes can be ruptured with electrical, optical, thermal, or other physical means.

Where multiple marker complexes are used, the marker in each complex may be the same or different.

A qualitative or semi-quantitative measurement of the presence or amount of an analyte of interest may be made with the unaided eye when visible dyes are used as the marker. The intensity of the color may be visually compared with a series of reference standards, such as in a color chart, for a semi-quantitative measurement. Alternatively, when greater precision is desired, or when the marker used necessitates instrumental analysis, the intensity of the marker may be measured directly on the membrane using a quantitative instrument such as a reflectometer, fluorimeter, spectrophotometer, electroanalyzer, etc.

Alternatively, the methods and test devices of the present invention may be modified to use an electrochemical marker. In the electrochemical detection method of the invention, an electroactive species, such as ferrocyanide, is encapsulated in the marker, e.g., liposomes. Electrodes are printed onto the membrane, or the membrane is placed in contact with reusable electrodes, such as an interdigitated electrode array. After lysis of the liposomes, the quantity of the electroactive species is determined.

Suitable electrochemical markers, as well as methods for selecting them and using them are disclosed, for example, in U.S. Pat. No. 5,789,154 to Durst et al., U.S. Pat. No. 5,756,362 to Durst et al., U.S. Pat. No. 5,753,519 to Durst et al., U.S. Pat. No. 5,958,791 to Roberts et al., U.S. Pat. No. 6,086,748 to Durst et al., U.S. Pat. No. 6,248,956 to Durst et al., U.S. Pat. No. 6,159,745 to Roberts et al., U.S. Pat. No. 6,358,752 to Roberts et al., and co-pending U.S. patent application Ser. No. 10/264,159, filed Oct. 2, 2002, which are hereby incorporated by reference in their entirety. Briefly, the test device may designed for amperometric detection or quantification of an electroactive marker. In this embodiment, the test device includes a working electrode portion(s), a reference electrode portion(s), and a counter electrode portion(s) on the membrane of the test device. The working electrode portion(s), reference electrode portion(s), and counter electrode portion(s) are each adapted for electrical connection to one another via connections to a potentiostat. Alternatively, the test device may be designed for potentiometric detection or quantification of an electroactive marker. In this embodiment, the test device includes an indicator electrode portion(s) and a reference electrode portion(s) on the membrane of the test device. The indicator electrode portions and reference electrode portions are adapted for electrical connection to potentiometers. In another embodiment, the test device may include an interdigitated electrode array positioned to induce redox cycling of an electroactive marker released from liposomes upon lysis of the liposomes.

Suitable electroactive markers are those which are electrochemically active but will not degrade the particles (e.g., liposomes) or otherwise leach out of the particles. They include metal ions, organic compounds such as quinones, phenols, and NADH, and organometallic compounds such as derivatized ferrocenes. In one embodiment, the electrochemical marker is a reversible redox couple. A reversible redox couple consists of chemical species for which the heterogeneous electron transfer rate is rapid and the redox reaction exhibits minimal overpotential. Suitable examples of a reversible redox couple include, but are not limited to, ferrocene derivatives, ferrocinium derivatives, mixtures of ferrocene derivatives and ferrocinium derivatives, cupric chloride, cuprous chloride, mixtures of cupric chloride and cuprous chloride, ruthenium-tris-bipyridine, potassium ferrohexacyanide, potassium ferrihexacyanide, and mixtures of potassium ferrohexacyanide and potassium ferrihexacyanide. Preferably, the electrochemical marker is encapsulated within a liposome, in the bilayer, or attached to a liposome membrane surface.

No membrane-immobilized binding material is required with the test devices adapted for electrochemical measurement in accordance with the invention.

The use of liposomes as described in the present application provides several advantages over traditional signal production systems employing, for example, enzymes. These advantages include increased signal intensity, shelf stability, and instantaneous release of signal-producing markers, as described in Siebert et al., *Analytica Chimica Acta* 282:297-305 (1993); Yap et al., *Analytical Chemistry* 63:2007 (1991); Plant et al., *Analytical Biochemistry* 176:420-426 (1989); Locascio-Brown et al., *Analytical Chemistry* 62:2587-2593 (1990); and Durst et al., Eds., *Flow Injection Analysis Based on Enzymes or Antibodies*, vol. 14, VCH, Weinheim (1990), each of which is hereby incorporated by reference in its entirety.

Liposomes can be prepared from a wide variety of lipids, including phospholipids, glycolipids, steroids, relatively long chain alkyl esters; e.g., alkyl phosphates, fatty acid esters; e.g.

lecithin, fatty amines, and the like. A mixture of fatty materials may be employed, such as a combination of neutral steroid, a charge amphiphile and a phospholipid. Illustrative examples of phospholipids include lecithin, sphingomyelin, and dipalmitoylphosphatidylcholine, etc. Representative steroids include cholesterol, chlorestanol, lanosterol, and the like. Representative charge amphiphilic compounds generally contain from 12 to 30 carbon atoms. Mono- or dialkyl phosphate esters, or alkylamines; e.g. dicetyl phosphate, stearyl amine, hexadecyl amine, dilaurylphosphate, and the like are representative.

The liposome sacs are prepared in aqueous solution containing the marker whereby the sacs will include the marker in their interiors. The liposome sacs may be prepared by vigorous agitation in the solution, followed by removal of the unencapsulated marker. Further details with respect to the preparation of liposomes are set forth in U.S. Pat. No. 4,342,826 and PCT International Publication No. WO 80/01515, both of which are hereby incorporated by reference in their entirety.

The solvent for the test mixture will normally be an aqueous medium, which may be up to about 40 weight percent of other polar solvents, particularly solvents having from 1 to 6, more usually of from 1 to 4, carbon atoms, including alcohols, formamide, dimethylformamide and dimethylsulfoxide, dioxane, and the like. Usually, the cosolvents will be present in less than about 30-40 weight percent. Under some circumstances, depending on the nature of the sample, some or all of the aqueous medium could be provided by the sample itself.

The pH for the medium will usually be in the range of 4-10, usually 5-9, and preferably in the range of about 6-8. The pH is chosen to maintain a significant level of binding affinity of the binding members and optimal generation of signal by the signal producing system. Various buffers may be used to achieve the desired pH and maintain the pH during the assay. Illustrative buffers include borate, phosphate, carbonate, tris, barbital, and the like. The particular buffer employed is usually not critical, but in individual assays, one buffer may be preferred over another. For nucleic acid analytes, it is necessary to choose suitable buffers. Such buffers include SSC, sodium chloride, sodium citrate buffer, and SSPE (sodium chloride, sodium phosphate, EDTA).

The concentration of electrolytes in the medium will usually be adjusted to achieve isotonicity or equi-osmolality (or up to about 50 to about 100 mmol/kg hypertonic) with the solution in the interior of liposomes to prevent their crenation or swelling.

With some increased complexity of the excitation waveform applied by the electroanalyzer, electrochemical measurement in accordance with the invention may also be carried out using stripping voltammetry, employing, for example, liposome encapsulated metal ions for detection and measurement.

Moderate, and desirably substantially constant, temperatures are normally employed for carrying out the assay. The temperatures for the assay and production of a detectable signal will generally be in the range of about 4-65° C., more usually in the range of about 20-38° C., and frequently, will be about 15-45° C.

The concentration, in the liquid sample, of analyte which may be assayed will generally vary from about $10^{-3}$ to about $10^{-20}$M, more usually from about $10^{-5}$ to $10^{-15}$M. Considerations such as the concentration of the analyte of interest and the protocol will normally determine the concentration of the other reagents.

With the test device and method of the invention, one may also assay a test sample for a plurality of analytes such as toxic chemicals or pathogens, or screen for one or more of a plurality of analytes. In one embodiment, the test device includes multiple capture portions, each of which is modified to bind a distinctive second binding material specific for one of several analytes. Thus, each analyte may be determined by assignment of each conjugate/analyte to its own measurement portion for concentration and measurement. Alternatively, the conjugate of each of the analytes to be determined in this embodiment of the invention, may include a marker which is detectable distinctly from the other markers. With different encapsulated dyes (e.g., fluorescent dyes) or quantum dots, the results of the assay can be "color coded". In particular, a multi-wavelength detector can be used in a capture portion.

As a matter of convenience, the present device can be provided in a kit in packaged combination with predetermined amounts of reagents for use in assaying for an analyte or a plurality of analytes. Aside from the universal marker complex having one member of a first coupling group immobilized thereto, universal marker complex having one member of a second coupling group immobilized thereto, and/or the universal membrane having a one member of a second coupling group immobilized at a capture portion, other additives such as ancillary reagents may be included, for example, stabilizers, buffers, and the like. Moreover, the kit may include a library of binding materials each modified with a member of a coupling group for selection and use with the universal marker complex(es) and the universal membrane after determination of the desired analyte(s) is made. The relative amounts of the various reagents may be varied widely, to provide for concentration in solution of the reagents which substantially optimizes the sensitivity of the assay. The reagents can be provided as dry powders, usually lyophilized, including excipients, which on dissolution will provide for a reagent solution having the appropriate concentrations for performing the assay. The kit or package may include other components such as standards of the analyte or analytes (analyte samples having known concentrations of the analyte).

The present invention is applicable to procedures and products for determining a wide variety of analytes. As representative examples of types of analytes, there may be mentioned: environmental and food contaminants, including pesticides and toxic industrial chemicals; drugs, including therapeutic drugs and drugs of abuse; hormones, vitamins, proteins, including enzymes, receptors, and antibodies of all classes; prions; peptides; steroids; bacteria; fungi; viruses; parasites; components or products of bacteria, fungi, viruses, or parasites; aptamers; allergens of all types; products or components of normal or malignant cells; etc. As particular examples, there may be mentioned $T_4$; $T_3$; digoxin; hCG; insulin; theophylline; leutinizing hormones; and organisms causing or associated with various disease states, such as streptococcus pyrogenes (group A), Herpes Simplex I and II, cytomegalovirus, chlamydiae, etc. The invention may also be used to determine relative antibody affinities, and for relative nucleic acid hybridization experiments, restriction enzyme assay with nucleic acids, binding of proteins or other material to nucleic acids, and detection of any nucleic acid sequence in any organism, i.e., prokaryotes and eukaryotes.

As described above, a device in accordance with the present invention can be used in a variety of assays, such as competitive binding assays and sandwich assays, as described in U.S. Pat. No. 5,789,154 to Durst et al., U.S. Pat. No. 5,756,362 to Durst et al., U.S. Pat. No. 5,753,519 to Durst et al., U.S. Pat. No. 5,958,791 to Roberts et al., U.S. Pat. No. 6,086,748 to Durst et al., U.S. Pat. No. 6,248,956 to Durst et al., U.S. Pat. No. 6,159,745 to Roberts et al., U.S. Pat. No. 6,358,752 to Roberts et al., co-pending U.S. patent application Ser. No. 09/698,564, filed Oct. 27, 2000, and co-pending U.S. patent application Ser. No. 10/264,159, filed Oct. 2, 2002, which are hereby incorporated by reference in their entirety.

As hereinabove indicated, the assay may be qualitative (presence or absence of certain level of target) or quantitative or semi-quantitative. The preparation of suitable standards and/or standard curves (the term "standard curve" is used in a generic sense to include a color chart) is deemed to be within the scope of those skilled in the art from the teachings herein.

The method of the invention, and preparation and use of the test device in accordance with the invention, are illustrated by the following Examples.

EXAMPLES

Example 1

Materials and Methods

Nucleotide Sequences Used in the Following Examples (all listed in the 5' to 3' direction)

Generic 20 nt liposome probe: CCA CCC CCA CCC CCA CCC CC (SEQ ID NO: 1)

E. coli specific reporter probes: GTC TGG TGA ATT GGT TCC GGG GGG TGG GGG TGG GGG TGG (SEQ ID NO: 2) and GTC TGG TGA ATT GGT TCC (biotinylated at 3' end) (SEQ ID NO: 3).

C. parvum specific reporter probe: GTG CAA CTT TAG CTC CAG TTG GGG GTG GGG GTG GGG GTG G (SEQ ID NO: 4).

Synthetic E. coli target sequence: GGC AAC CGT GTC GTT TAT CAG ACC ACT TAA CCA AGG C (SEQ ID NO: 5).

Synthetic C. parvum target sequence: A CCA GCA TCC TTG AGC ATT TTC TCA ACT GGA GCT AAA GTT GCA CGG AAG TAA TCA GCG CAG AGT TCT TCG AAT CTA GCT CTA CTG ATG GCA ACT GAA (SEQ ID NO: 6).

Capture probes are either biotinylated or tagged with fluorescein at 5' end: E. coli specific capture probe: CCG TTG GCA CAG CAA ATA (SEQ ID NO: 7); C. parvum specific capture probe: AGA TTC GAA GAA CTC TGC GC (SEQ ID NO: 8).

Liposome Preparation

Liposomes were prepared using the reversed-phase evaporation method. Lipids used to prepare the liposomes included: 40.3 μmol dipalmitoyl phosphatidylcholine (DPPC), 21.0 μmol dipalmitoyl phosphatidylglycerol (DPPG) and 51.7 μmol cholesterol. 7.2 μmol (5 mg) of diphosphatidyl palmitoylethanolamine (DPPE) was first dissolved in 1 mL of 0.7% triethylamine (v/v) in chloroform by sonicating for one minute in a round-bottom flask. 14.3 μmol (3.5 mg) of N-succinimidyl-5-acetylthioacetate (SATA) was allowed to react with DPPE forming DPPE-ATA, which was incorporated into the bilayer of the liposomes. The lipids were combined in 6.5 mL of a mixture of chloroform, isopropyl ether, and methanol in a 6:6:1 ratio. Liposomes formed when the organic solvent was boiled off in a roto-evaporator. 150 mM Sulforhodamine B was dissolved in phosphate buffer, pH 7.5, and entrapped in the liposomes. Subsequently, the liposomes were extruded through 0.4 μm and then 0.2 μm polycarbonate filters for sizing using the Avanti mini-extruder and polycarbonate filters (Avanti Polar Lipids, Alabaster, Ala.). Liposomes were purified from free dye by gel filtration using Sephadex G50 columns followed by dialysis against 0.1 M PBS buffer, pH 7.0, with an osmolarity 75 mmol/kg higher than the osmolarity of the encapsulant solution. The osmolarity was adjusted using sucrose.

Example 2

Immobilization of Streptavidin on a Liposome Surface

To couple streptavidin to the liposomes, an activated lipid (DPPE-ATA) was incorporated into the liposomes. Streptavidin was first dissolved in 0.05 M potassium phosphate buffer, pH 7.8, containing 1 mM ethylenediaminetetraacetic acid (EDTA) to a concentration of 100 nmol/mL, to prepare for conjugation to the liposome surface. N-(κ-maleimidoundecanoyloxy) sulfosuccinimide ester (sulfo-KMUS) was then dissolved in dimethylsulfoxide (DMSO) to a concentration of 20.8 μmol/L. 4.3 μL of this stock was added to 100 μL of the streptavidin solution and allowed to react at room temperature in a shaker for 2 to 3 hours.

Second, the thiol groups on the streptavidin were deprotected by deacetylation of the acetylthioacetate groups. This was accomplished by mixing the streptavidin with a hydroxylamine hydrochloride solution, pH 7.5, containing 0.5 M hydroxylamine hydrochloride, 25 mM EDTA, and 0.4 M phosphate buffer. 28.73 μl of solution was added to the ATA-streptavidin solution such that the final concentration of hydroxylamine was 0.05 M. This mixture was incubated at room temperature for 2 hours on a shaker.

Finally, the SH-streptavidin was allowed to react with the maleimide tagged liposomes. The desired density of streptavidin used was for example 0.12 mol % of the total lipid. The SH-streptavidin were incubated at room temperature with the liposomes for 3 to 4 hours and then overnight at 4° C. Liposomes were reacted with cysteine in PBS buffer at 10× the molar concentration of maleimide in order to cap all the unconjugated maleimide groups. The liposomes were purified from free streptavidin on a Sepharose CL-4B column and then dialyzed in 0.1 M PBS buffer, pH 7.0, plus sucrose with osmolarity of 617 mmol/kg overnight in the dark. Liposomes were stored in the dark at 4° C.

Example 3

Immobilization of a Generic Oligonucleotide on a Liposome Surface

For the generic probe (SEQ ID NO: 1, above) (5' end modified with an amine group) and specific reporter probes (E. coli: SEQ ID NO: 3, above; C parvum: 5' GTG CAA CTT TAG CTC CAG TT 3' (SEQ ID NO: 9); B. anthracis: 5' CAA GAT GTC CGC GTA TTT AT 3' (SEQ ID NO: 10)) (3' end modified with an amine group), the same protocol as described in Example 2 was followed, using 100 nmol/mL solutions of the oligonucleotides.

Example 4

Immobilization of Streptavidin on Polyethersulfone Membranes

Polyethersulfone membranes from Pall/Gelman Company were cut into 4.5×55 mm strips and coated with streptavidin for use with the original universal biosensor. 15 μmol streptavidin in 0.4 M $Na_2CO_3$/$NaHCO_3$ buffer, pH 9.0, containing 5% methanol was pipetted onto each membrane. These were dried at room temperature for 10 minutes then in a vacuum oven (15 psi) at 50-55° C. for 1.5 hours. The membranes were subsequently blocked with a blocking reagent of 0.5% polyvinylpyrrolidone, 0.015% casein in Tris buffered saline (TBS: 20 mM Tris, 150 mM NaCl, 0.01% $NaN_3$, pH 7-7.5) for 30 minutes. The membranes were blotted dry, air dried in a fume hood for 10 minutes, and then in the vacuum oven (15 psi) at 25-30° C. for 2 hours. The membrane strips were stored in vacuum-sealed bags at 4° C. until use.

Example 5

Immobilization of Anti-Fluorescein Antibody to Polyethersulfone Membranes

Anti-fluorescein antibody membranes which contained anti-fluorescein antibody in the capture zone instead of streptavidin were produced, as described in Example 4. 15 µmol of antibody in 0.4 M $Na_2CO_3/NaHCO_3$ buffer, pH 9.0, containing 5% methanol was pipetted onto each membrane as an initial investigation. All other procedures followed the protocol described in Example 4.

Example 6

Bioassay Using Universal Liposomes with Generic Oligonucleotides of Different Lengths Liposomes were modified to include generic oligonucleotides containing mainly dC of different lengths, i.e., 17 nt, 20 nt, 25 nt, and 30 nt on their surfaces, as described in Example 3. The corresponding *E. coli* specific reporter probes were modified to bear a 17-30 nt long oligo dG (with some dA or dT) at their 3' end. The sequences of generic probes and reporter probes used were as follows:

TABLE 1

Generic Probes and Modified *E. coli* Specific Reporter Probes

| 5' to 3' | |
|---|---|
| gtc tgg tga att ggt tcc ggg ggt ggg ggt ggg gg (SEQ ID NO:11) | 17 nt reporter probe |
| ccc cca ccc cca ccc cc (SEQ ID NO:12) | liposome probe |
| gtc tgg tga att ggt tcc ggg ggt ggg ggt ggg ggt gg (SEQ ID NO:13) | 20 nt reporter probe |
| cca ccc cca ccc cca ccc cc (SEQ ID NO:1) | liposome probe |
| gtc tgg tga att ggt tcc ggg ggt ggg ggt ggg ggt ggg g (SEQ ID NO:14) | 25 nt reporter probe |
| cac ccc cac ccc cac ccc cac ccc c (SEQ ID NO:15) | liposome probe |
| gtc tgg tga att ggt tcc ggg ggt ggg ggt ggg ggt ggg ggt (SEQ ID NO:16) | 30 nt reporter probe |
| acc ccc acc ccc acc ccc acc ccc acc ccc (SEQ ID NO:17) | liposome probe |

Figure 3:
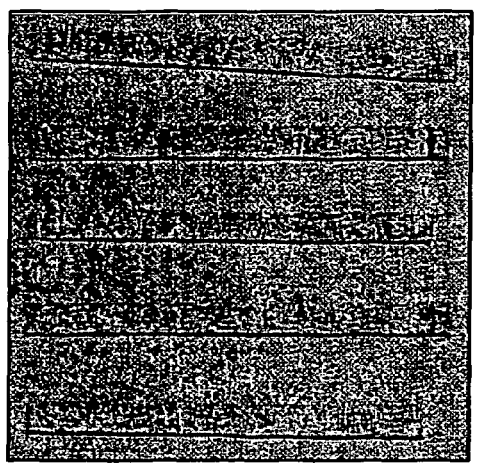
FIG. 3 is a graph showing the optimization of generic oligonucleotide coupling group length. Generic oligonucleotides (17-30 nucleotides long) were immobilized on a liposome surface. *Escherichia coli* specific reporter probes were modified with the complementary sequence at their 5' end to bind to the generic oligonucleotides. Modified liposomes and modified *E. coli*-specific reporter probes were incubated with the target sequence for 10 minutes at 41° C. and were subsequently used in the biosensor assay.

2 µL of liposomes, 0.457 µL of reporter probes (2 pmol/µL dissolved in $NaHCO_3/Na_2CO_3$ buffer, 0.4 M, pH 9.0.), 1.0 µL of target sequence (1 pmol/µL) (SEQ ID NO: 5), and 8.54 µL of master mix (20% formamide, 5×SSC, 0.2% Ficoll type 400, 0.2M sucrose) were incubated for 10 minutes at 41° C. The membrane was inserted in the mixture and then 50 µL of running buffer (20% formamide, 5×SSC, 0.2% Ficoll type 400, 0.2M sucrose) was added. The mixture was allowed to run all the way to the top of the membrane, the membrane was removed from the mixture, and was allowed to dry. A reflectometer reading was then taken using a BR-10 reflectometer (λ=560 nm) (ESECO, Cushing, Okla.). The results are shown in FIG. 3. As shown in FIG. 3, the generic probes of 20 nt were optimal.

Example 7

Figure 4:
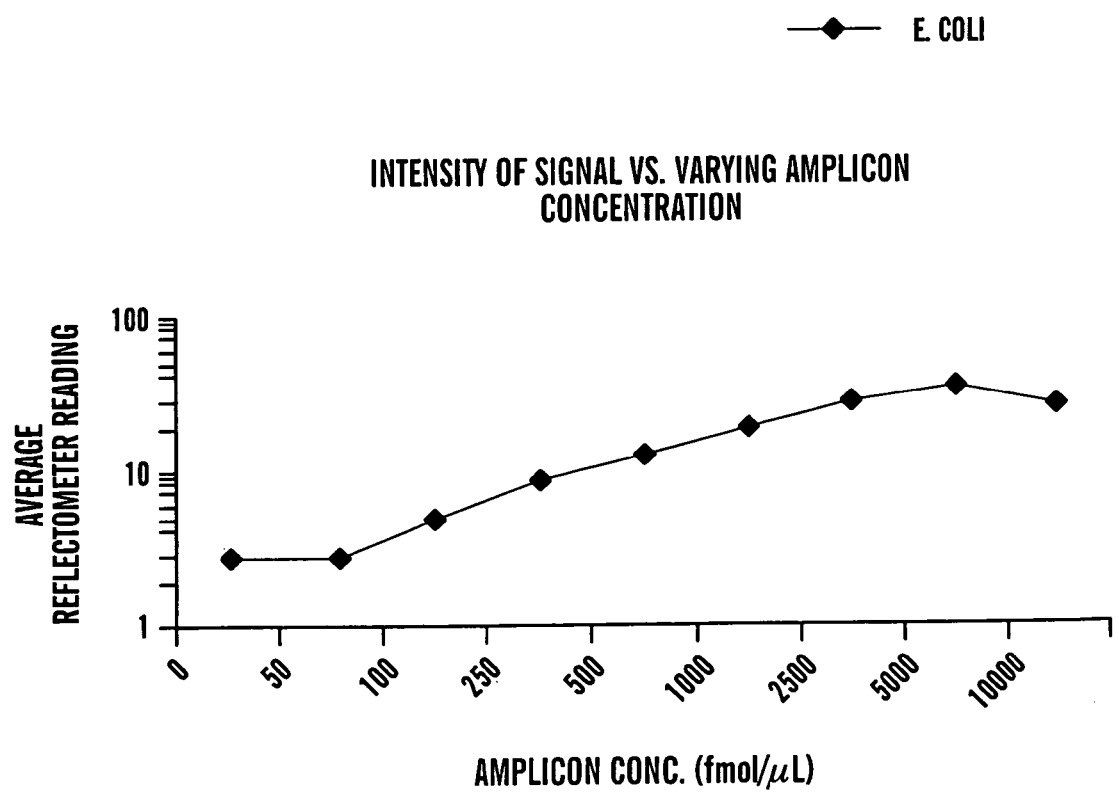
FIG. 4 is a graph showing the results of signal strength versus varying concentrations of *E. coli* target sequence using universal liposomes bearing a generic oligonucleotide hybridized to a modified *E. coli*-specific reporter probe.
Figure 5:
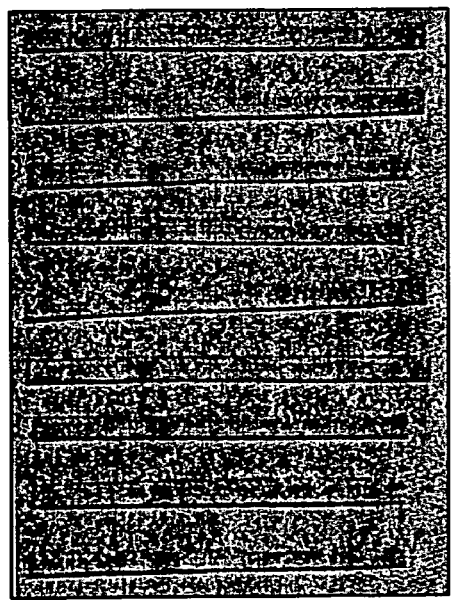
FIG. 5 shows the results of signal strength versus varying concentrations of *Cryptosporidium parvum* target sequence using universal liposomes bearing a generic oligonucleotide hybridized to a modified *C. parvum*-specific reporter probe.

Determination of Limit of Detection Using 20 Nucleotide Generic Oligonucleotides and Specific *Escherichia coli/Cryptosporidium Parvum* Reporter Probes Universal liposomes modified to include generic oligonucleotides were also used to investigate the limit of detection using 20 nt long generic probes (SEQ ID NO: 1) on the liposome surface and specific *E. coli* reporter probes (SEQ ID NO: 2) as well as specific *C. parvum* reporter probes (SEQ ID NO: 4). In particular, 2 µL of liposomes, 0.286 µL reporter probes with a 20 nt long generic part (2 µmol/µL dissolved in $NaHCO_3/Na_2CO_3$ buffer, 0.4 M, pH 9.0.), 1.0 µL of target sequence (1 pmol/µL) (SEQ ID NOS: 5 and 6), and 8.71 µL of master mix (15% formamide, 5×SSC, 0.1% Ficoll type 400, 0.2M sucrose) were incubated for 10 minutes at 41° C. The membrane was inserted in the mixture, then 50 µL running buffer (20% formamide, 8×SSC, 0.2% Ficoll 400, 2M sucrose) was added. The mixture was allowed to run all the way to the top of the membrane, the membrane was removed from the mixture, and was allowed to dry. Reflectometer readings were then taken (BR-10 Reflectometer (λ=560 nm), ESECO, Cushing, Okla.). Different concentrations of target sequence (*E. coli* and *C. parvum*) were investigated as shown in FIG. 4 with the example of *E. coli* and in FIG. 5 with the example of *C. parvum*. A detection limit of as low as 100 fmol was established for *E. coli* and as low as 50 fmol for *C. parvum* (10 times above the specific biosensor assay).

Example 8

Combination of Universal Liposomes of Example 3 with *E. coli* Specific Membranes—Optimization of Probe Tag on Liposomes An incubation mixture including 2.0 µL liposomes, surface tag (SEQ ID NO: 1) varied with each assay as follows: 0.1 mol %, 0.2 mol %, 0.4 mol %, and 0.6 mol % surface tag, 1.0 µL reporter probe (SEQ ID NO: 2) at a concentration of 2 pmol/µL, 1.0 µL synthetic target sequence (SEQ ID NO: 5) at a concentration of 500 fmol/µL, and 4.0 µL master mix (20% formamide, 4×SSC, 0.4% Ficoll, 0.4 M sucrose) was prepared in a glass culture tube. The mixture was incubated in the glass test tube for 15 minutes in a water bath at 41° C. The mixture was removed from the bath, and one *E. coli*-specific membrane strip was inserted in each mixture.

To produce the *E. coli*-specific membrane strip, polyethersulfone membranes were cut into strips of 4.5×80 mm. Subsequently, the membranes were coated with a mixture of streptavidin and biotinylated capture probes (SEQ ID NO: 7). A mixture containing 15 pmol streptavidin and 45 pmol capture probe per µL in a sodium carbonate buffer (0.4 M $NaHCO_3/NA_2CO_3$ with 5% methanol) was incubated for at least 15 minutes at room temperature. The streptavidin-capture probe mixture was immobilized on the membrane strips by pipetting 1 μL of the mixture directly onto the membrane, approximately 2.5 cm from the bottom. The membranes were dried for 5 minutes at room temperature and then for an additional 1.5 hours in a vacuum oven (15 psi) at 52 to 55° C. Subsequently, the membranes were incubated in a blocking solution of 0.5% polyvinylpyrrolidone, 0.015% casein in Tris buffered saline (TBS: 20 mM Tris, 150 mM NaCl, 0.01% NaN$_3$, pH 7 to 7.5) for 30 minutes. The membranes were blotted dry and finally dried in the vacuum oven (15 psi) at 30° C. for 2 hours. They were stored in vacuum-sealed bags at 4° C. until use.

Figure 6:
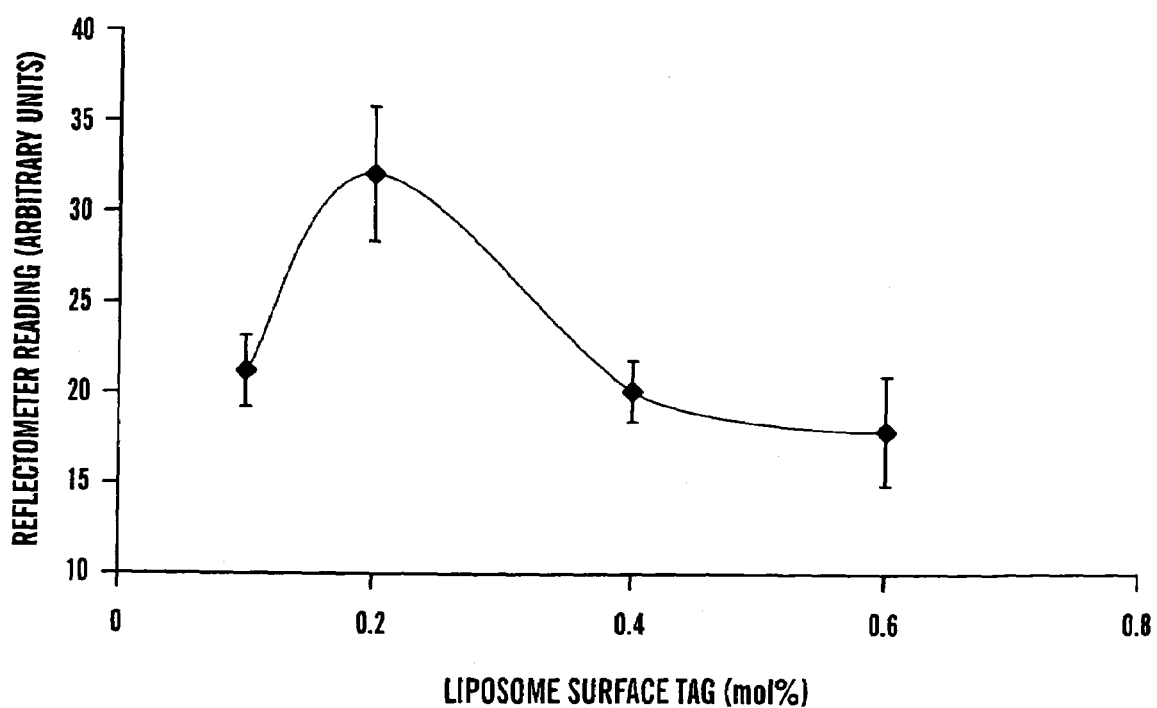
FIG. 6 is a graph showing the results from assays that used liposomes containing 0.1, 0.2, 0.4, and 0.6 mol % generic oligonucleotide tags. Each data point represents an average of five identical assays. 500 fmol of target sequence were used in each assay.

The entire incubation mixture was allowed to be absorbed by the membrane. An additional 40 μL of the prepared running buffer (20% formamide, 5×SSC, 0.2% Ficoll, 0.2 M sucrose) was added to the culture tube, and was allowed to fully run the length of the membrane. The membrane strips were allowed to dry and the resulting signal at the capture zone was measured using a reflectometer (BR-10 Reflectometer ($\lambda$=560 nm), ESECO, Cushing, Okla.). The results are shown in FIG. 6. It was found that 0.2 mol % tag of generic probe on the liposome was optimal under the assay conditions.

Example 9

Figure 7:
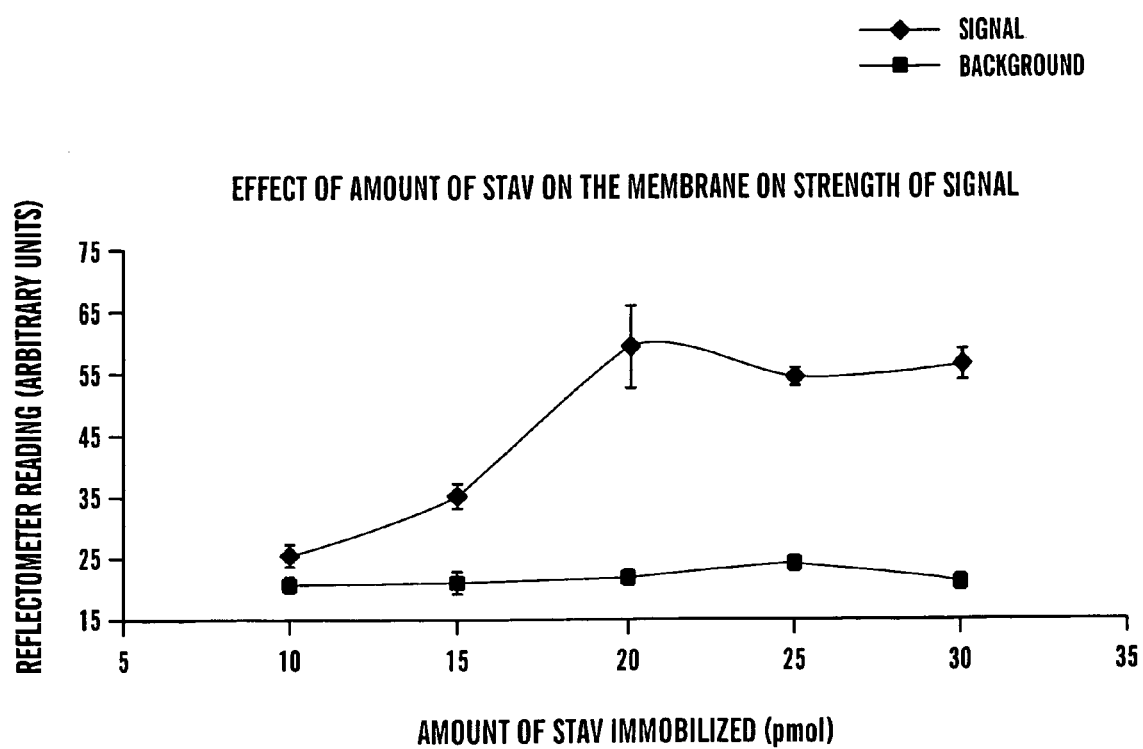
FIG. 7 is a graph showing the effect of the amount of streptavidin on a polyethersulfone membrane on the strength of the signal. Streptavidin amounts of 10, 15, 20, 25, and 30 μmol were investigated using 500 fmol of target sequence.

Combination of Membranes with Immobilized Streptavidin and Liposomes Tagged with a Generic Probe—Optimization of the Streptavidin Concentration on the Polyethersulfone Membrane An incubation mixture including 2 μL liposomes (0.1 mol % tag (SEQ ID NO: 1), absorbance 1:400 diluted at 532 nm=0.103), 1 μL reporter probe (SEQ ID NO: 2) at 2 pmol/μL, 1 μL target sequence (SEQ ID NO: 5) at 500 fmol/μL, and 5 μL master mix (20% formamide, 4×SSC, 0.4% Ficoll 400, 0.4 M sucrose) was prepared. The mixture was incubated in a glass tube for 20 minutes at 41° C. 1 μL of capture probe (SEQ ID NO: 7) at 1 μmol/μL was added. The mixture was then incubated again for 20 minutes at 41° C. Membranes were inserted into the test tube, with each membrane varying with the amount of streptavidin immobilized thereto (10μ, 15, 20, 25, and 30 pmol). Three replicates of each type of membrane were run. Subsequently, 38 μL of running buffer (20% formamide, 5×SSC, 0.2% Ficoll 400, 0.2 M sucrose) was added. Negative controls (with water instead of target) were run for each type of membrane. It was found that 20 μmol of streptavidin immobilized on the membrane was optimal under the given assay conditions (FIG. 7).

Example 10

Figure 8:
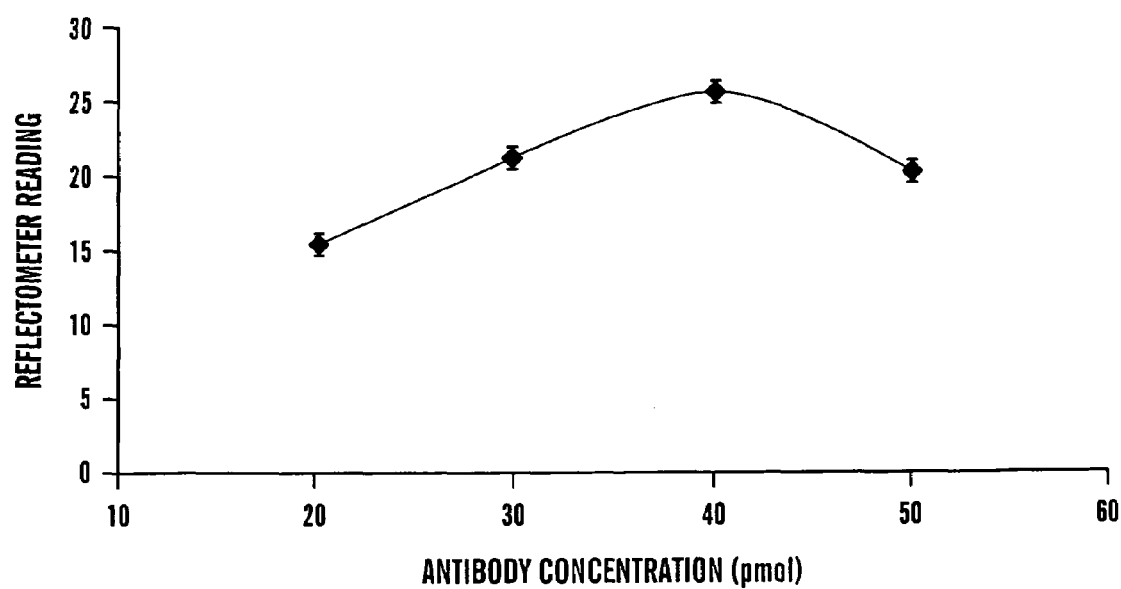
FIG. 8 is a graph showing the effect of anti-fluorescein antibody concentration immobilized on polyethersulfone membranes. The assay included 5 μmol fluoresceinated capture probe, 2 μL liposomes tagged with streptavidin, 2 μmol biotinylated reporter probes, and 2 μmol target sequence.

Combination of Antibody Immobilized on Membranes and Liposomes with Streptavidin—Optimization of the Antibody Concentration on the Membrane Using *E. coli* Sequences as Model Analytes 5 μL total volume was mixed in a glass tube containing 2 μL universal liposomes (with immobilized streptavidin), 1 μL target sequence (SEQ ID NO: 5), 0.5 μL each of reporter probe (SEQ ID NO: 3) and capture probe (SEQ ID NO: 7), and 1 μL hybridization buffer (45% formamide, 9×SSC, 0.6 M sucrose and 0.6% Ficoll type 400). The components were left to hybridize by incubating the mixture at 41° C. for 10 minutes. Subsequently, the membrane with varying concentrations of immobilized anti-fluorescein antibody (20, 30, 40, and 50 pmol) was inserted into the glass tube and the mixture was allowed to migrate up the membrane. As soon as all of the mixture was absorbed by the membrane, 40 μL of running buffer (30% formamide, 6×SSC, 0.2M sucrose, 0.4% Ficoll type 400) was added to the tube. Once the solution reached the end of the membrane, the strips were removed from the glass tube and air dried prior to taking the measurement with the reflectometer. The results are shown in FIG. 8, with 40 μmol anti-fluorescein antibody determined to be the optimal concentration in the assay conditions employed.

Example 11

Combination of Antibody Immobilized on Membranes and Liposomes Tagged with Streptavidin—Optimization of Reporter Probe Concentration for *E. coli* Detection An incubation mixture including 1 μL master mix (45% formamide, 10×SSC, 0.6M sucrose, 0.6% Ficoll type 400), 2 μL liposomes (0.2 mol % tag of streptavidin on liposomes), 0.5 μL reporter probe (SEQ ID NO: 3) (varied from 0-10 pmol), 1 μL target (SEQ ID NO: 5) (1 pmol), and 0.5 μL capture probe (SEQ ID NO: 7) (4 pmol) was prepared. The mixture was incubated at 42° C. for 30 minutes. The assay was run with 32 μL of running buffer (30% formamide, 6×SSC, 0.2M sucrose, 0.4% Ficoll type 400). The membranes used in this experiment had 30 pmol anti-fluorescein immobilized on the capture zone and were blocked with 0.015% Casein in 1×TBS and 0.5% PVP.

Figure 9:
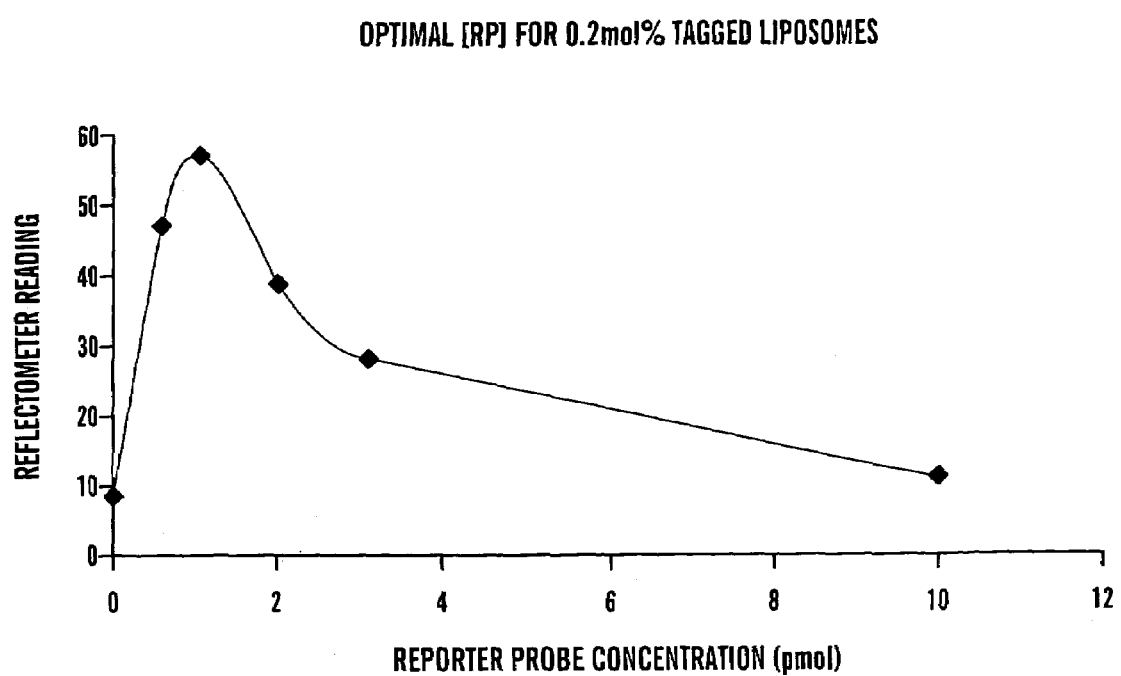
FIG. 9 is a graph showing the optimization of reporter probe concentration for *E. coli* detection using polyethersulfone membranes including immobilized antibody and liposomes tagged with streptavidin.

Eleven total assays were run: one at 0 pmol reporter probe, two at 500 fmol reporter probe, two at 1 pmol reporter probe, two at 2 pmol reporter probe, two at 3 pmol reporter probe, and two at 10 pmol reporter probe (see FIG. 9). 1 pmol was determined to be the optimal reporter probe concentration for 0.2 mol % tagged liposomes.

Example 12

Combination of Membranes with Immobilized Streptavidin And Liposomes Tagged with a Generic Oligonucleotide—Determination of Detection Limit and Range for Detection of *E. coli* (clpB Synthetic Target Sequence), *B. anthracis* (Atxa Synthetic Target Sequence), and *C. parvum* (Hsp70 Synthetic Target Sequence)

An incubation mixture including 2 μL liposomes (0.2 mol % tag), 1 μL reporter probe at 2 pmol/μL, 1 μL synthetic target sequence (*E. coli* clpB synthetic target sequence, *B. anthracis* atxA synthetic target sequence, or *C. parvum* hsp70 synthetic target sequence) at varying concentrations (see FIGS. 10-12), and 5 μL master mix (20% formamide, 4×SSC, 0.4% Ficoll 400, 0.4 M sucrose) was prepared. The mixture was incubated in a glass tube for 20 minutes at 41° C. 1 μL of capture probe at 1 pmol/μL was added. The mixture was then incubated again for 20 minutes at 41° C. A membrane was inserted into the test tube, with the membrane including 20 μmol of streptavidin immobilized thereto. Subsequently, 38 μL of running buffer (20% formamide, 5×SSC, 0.2% Ficoll 400, 0.2 M sucrose) was added. Negative controls (with water instead of target) were run for each target sequence.

Figure 10:
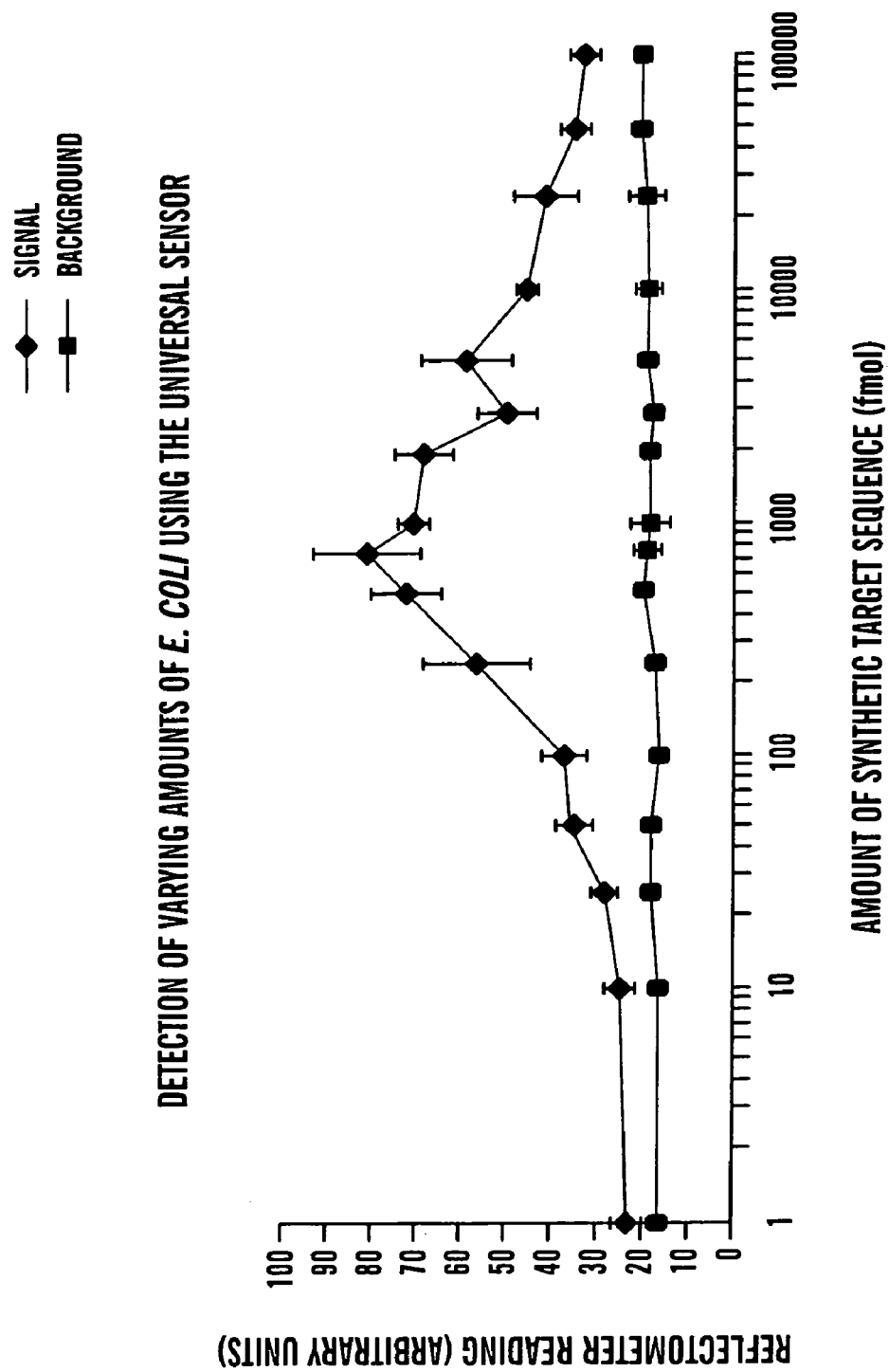
FIG. 10 is a graph showing the determination of the detection limit and dynamic range of a universal biosensor of the present invention (using streptavidin immobilized on membranes and liposomes tagged with a generic oligonucleotide probe) for the detection of *E. coli* (clpB synthetic target sequence).

The following sequences were used for determining the detection limit and dynamic range of the universal biosensor for detection of *E. coli*: synthetic target sequence: SEQ ID NO: 5; generic 20 nt liposome probe: SEQ ID NO: 1; capture probe: SEQ ID NO: 7; and reporter probe: SEQ ID NO: 3. The results for *E. coli* clpB synthetic target sequence are shown in FIG. 10. The detection limit was determined to be 10 fmol per assay, and the dynamic range was 10 fmol to 750 fmol.

The following sequences were used for determining the detection limit and dynamic range of the universal biosensor for detection of *B. anthracis*:

TABLE 2

| Sequences used (written in 5'-3'). | |
| --- | --- |
| Synthetic atxA target sequence | AT AAA TAC GCG GAC ATC TTG TC TTC TCT TCC CGA TAT TTC TAG (SEQ ID NO:18) |
| Generic 20 nt liposome probe | CCA CCC CCA CCC CCA CCC CC (SEQ ID NO:1) |
| Capture Probe | CTA GAA ATA TCG GGA AGA GAA (SEQ ID NO:19) |
| Reporter Probe | CAA GAT GTC CGC GTA TTT AT GGG GGG TGG GGG TGG GGG TGG (SEQ ID NO:20) |

Figure 11:
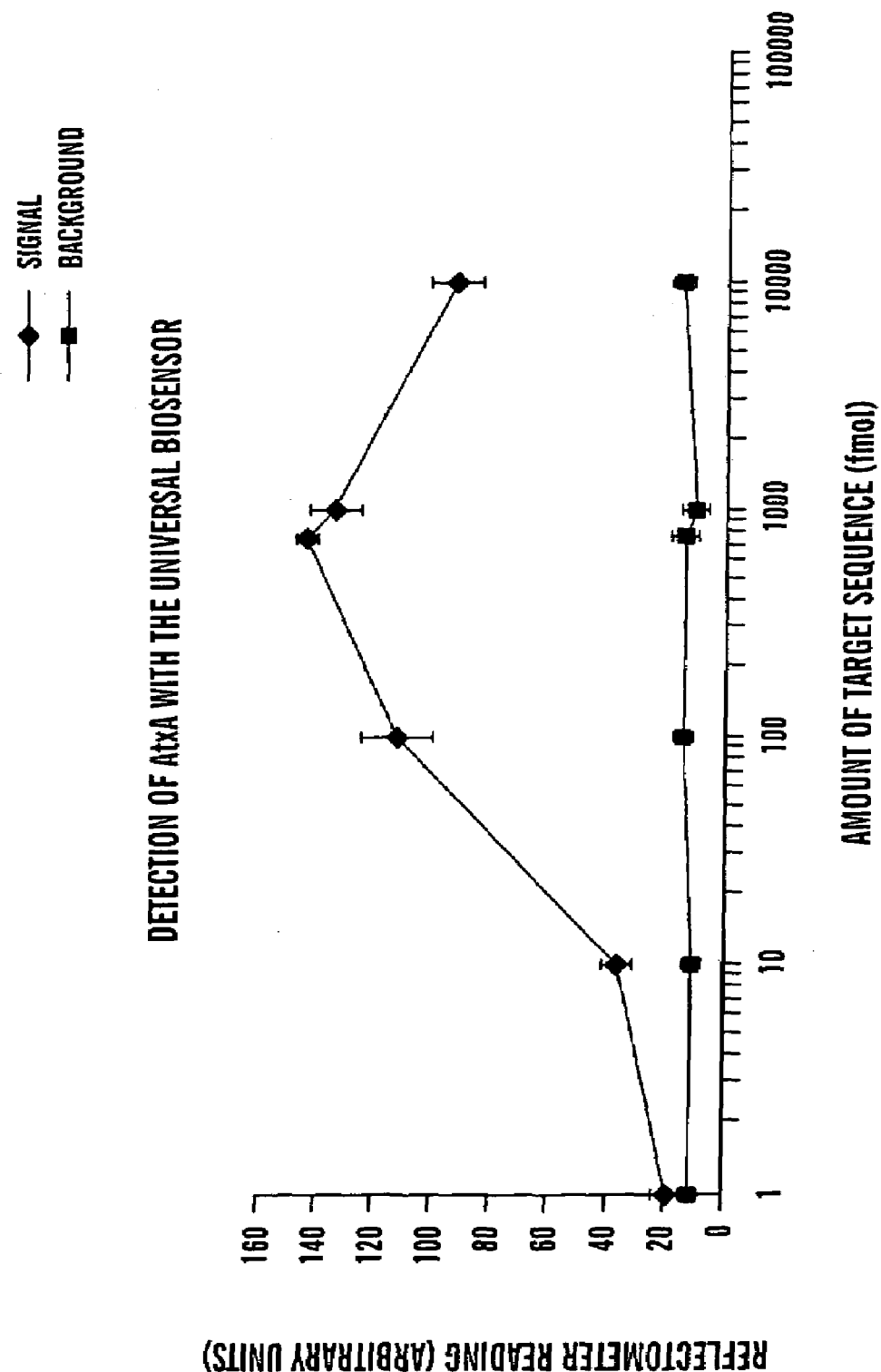
FIG. 11 is a graph showing the determination of the detection limit and dynamic range of a universal biosensor of the present invention (using streptavidin immobilized on membranes and liposomes tagged with a generic oligonucleotide probe) for the detection of *B. anthracis* (atxA synthetic target sequence).

The results for *B. anthracis* atxA synthetic target sequence are shown in FIG. 11. The detection limit was determined to be 10 fmol per assay, and the dynamic range was 10 fmol to 750 fmol.

The following sequences were used for determining the detection limit and dynamic range of the universal biosensor for detection of *C. parvum*:

TABLE 3

| Sequences used (written in 5'-3'). | |
| --- | --- |
| Synthetic hsp70 target sequence | A CCA GCA TCC TTG AGC ATT TTC TCA ACT GGA GCT AAA GTT GCA CGG AAG TAA TCA GCG CAG AGT TCT TCG AAT CTA GCT CTA CTG ATG GCA ACT GAA (SEQ ID NO:21) |
| Generic 20 nt liposome probe | CCA CCC CCA CCC CCA CCC CC (SEQ ID NO:1) |
| Capture Probe | AGA TTC GAA GAA CTC TGC GC (SEQ ID NO:22) |

TABLE 3-continued

| Sequences used (written in 5'-3'). | |
| --- | --- |
| Reporter Probe | GTG CAA CTT TAG CTC CAG TTG GGG GTG GGG GTG GGG GTG G (SEQ ID NO:23) |

Figure 12:
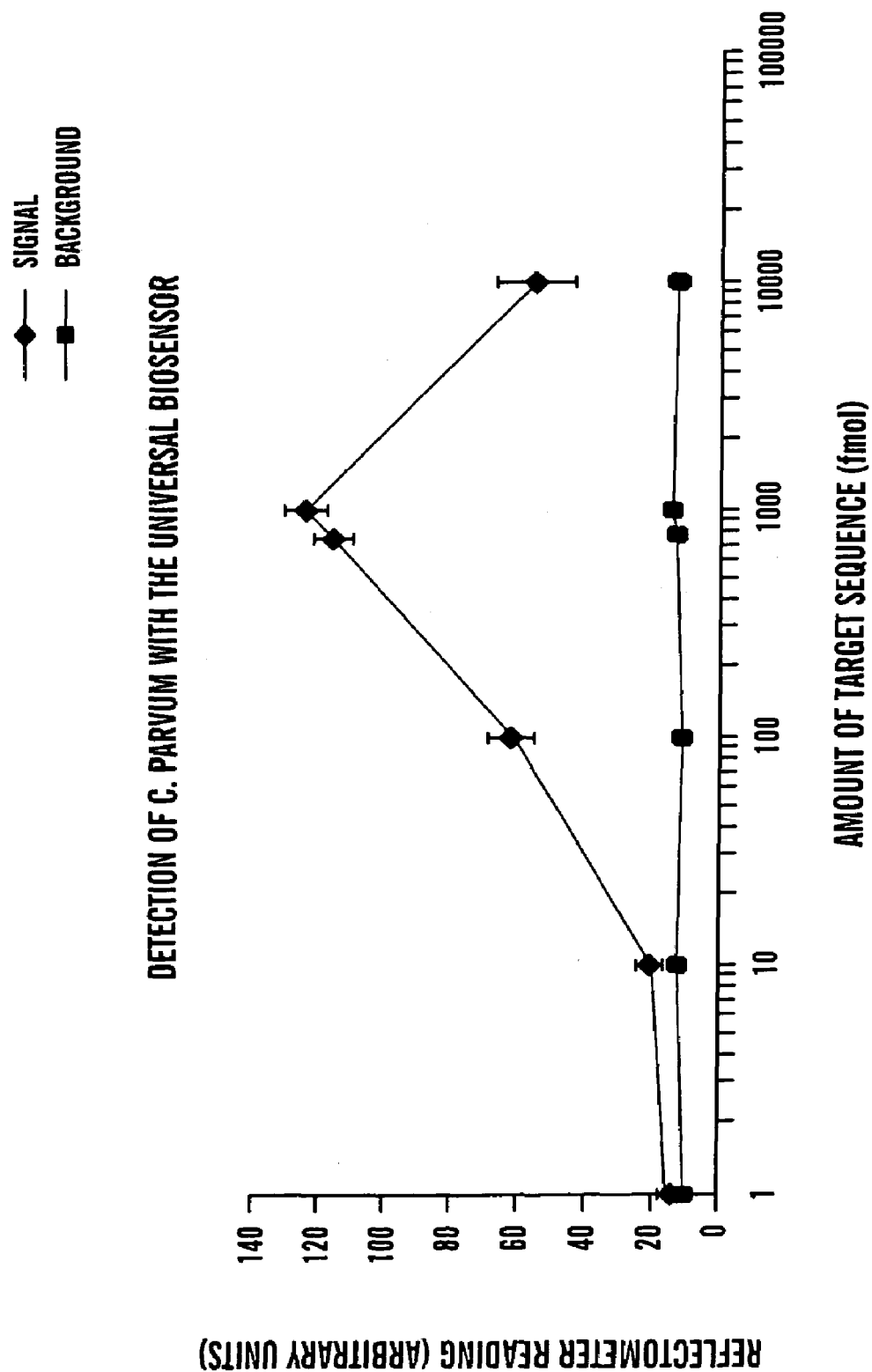
FIG. 12 is a graph showing the determination of the detection limit and dynamic range of a universal biosensor of the present invention (using streptavidin immobilized on membranes and liposomes tagged with a generic oligonucleotide probe) for the detection of *C. parvum* (hsp70 synthetic target sequence).

The results for C parvum hsp70 synthetic target sequence are shown in FIG. 12. The detection limit was determined to be 10 fmol per assay, and the dynamic range was 10 fmol to 1000 fmol.

Example 13

Combination of Antibody Immobilized on Membranes and Liposomes Tagged with Streptavidin—Optimization of Formamide Concentration in Master Mix for Detection of *E. coli* Target Sequence (Synthetic clpB)

An incubation mixture including 1 μL master mix (0-55% formamide, 10×SSC, 0.6M sucrose, 0.6% Ficoll type 400), 2 μL liposomes (0.2 mol % tag of streptavidin on liposomes), 0.5 μL reporter probe (SEQ ID NO: 3) (1 pmol), 1 μL target (SEQ ID NO: 5) (500 fmol), and 0.5 μL capture probe (SEQ ID NO: 7) (4 pmol) was prepared. The mixture was incubated at 42° C. for 20 minutes. The assay was run with 32 μL of running buffer (30% formamide, 4×SSC, 0.2M sucrose, 0.4% Ficoll type 400). The membranes used in this experiment had 30 μmol anti-fluorescein immobilized on the capture zone and were blocked with 0.015% Casein in 1×TBS and 0.5% PVP.

Figure 13:
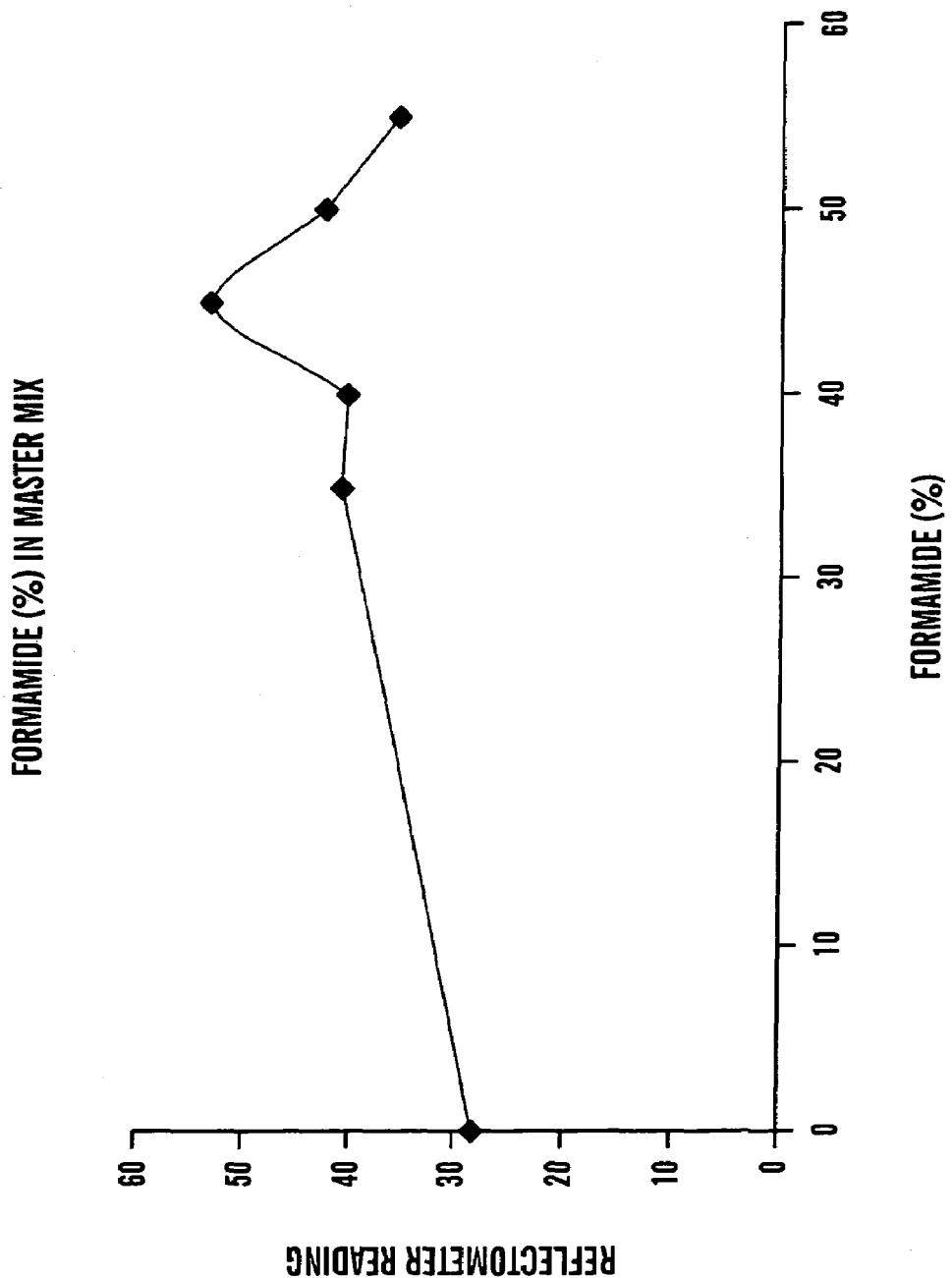
FIG. 13 is a graph showing the determination of the optimal formamide concentration in the master mix for the universal biosensor of the present invention (using anti-fluorescein antibody immobilized on membranes and liposomes tagged with streptavidin) for the detection of *E. coli* (clpB synthetic target sequence).

Eighteen total assays were run: three at 0% formamide, three at 35% formamide, three at 40% formamide, three at 45% formamide, three at 50% formamide, and three at 55% formamide (see FIG. 13). 45% formamide was determined to be the optimal formamide concentration in the master mix.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method for detecting or quantifying an analyte in a test sample comprising:
   providing at least one test mixture comprising:
   a test sample, wherein the test sample potentially contains an analyte;
   a marker complex, wherein the marker complex comprises a particle, a marker, and a first member of a first coupling group;
   a first binding material, wherein the first binding material is selected to bind with a portion of the analyte and wherein the first binding material comprises a second member of the first coupling group; and
   a second binding material, wherein the second binding material is selected to bind with a portion of the analyte other than the portion of the analyte for which the first binding material is selected and wherein the second binding material comprises a first member of a second coupling group;
   contacting the at least one test mixture with a surface having a second member of the second coupling group immobilized thereto;
   permitting reaction to occur between any analyte present and the first and second binding materials, between the first and second members of the first coupling group, and between the first and second members of the second coupling group;
   detecting the presence or amount of the marker on the surface using a detection assembly; and
   correlating the presence or amount of the marker on the surface with the presence or amount, respectively, of the analyte in the test sample;
   wherein the first and second members of the first coupling group and the first and second members of the second coupling group are capable of recognizing a particular spatial and polar organization of the other member of its respective coupling group.

2. The method according to claim 1, wherein contacting comprises contacting a single mixture including the test sample, the marker complex, the first binding material, and the second binding material.

3. The method according to claim 1, wherein said contacting comprises contacting two or more mixtures each including one or more of the test sample, the marker complex, the first binding material, and the second binding material.

4. The method according to claim 3, wherein the two or more mixtures are passed sequentially.

5. The method according to claim 4, wherein a test mixture comprising the second binding material is contacted with the surface under conditions effective to permit reaction between the first and second members of the second coupling group and subsequently a test mixture comprising the test sample, the marker complex, and the first binding material is contacted with the surface.

6. The method according to claim 3, wherein the two or more mixtures are contacted substantially simultaneously.

7. The method according to claim 1, wherein reaction between any analyte present and the first and second binding materials and reaction between the first and second members of the first coupling group occurs in the at least one test mixture prior to contacting the at least one test mixture with the surface.

8. The method according to claim 1, wherein reaction between any analyte present and the first and second binding materials and reaction between the first and second members of the first coupling group occurs on the surface.

9. The method according to claim 1, wherein the surface comprises a contact portion on a first absorbent material and a capture portion either on said first absorbent material, or on a second absorbent material in fluid flow contact with said first absorbent material, and wherein the second member of the second coupling group is bound to the capture portion.

10. The method according to claim 9, wherein contacting comprises allowing the test mixture to migrate from the contact portion to the capture portion.

11. The method according to claim 1, wherein the surface comprises a filtration membrane.

12. The method according to claim 1, wherein each of said first and second binding materials is an antibody, an antigen, a nucleic acid sequence, an aptamer, or a cell receptor.

13. The method according to claim 1, wherein said first and second coupling groups are selected from the group consisting of antibody-antigen, receptor-ligand, biotin-streptavidin, sugar-lectins, and complementary oligonucleotides.

14. The method according to claim 1, wherein said analyte is a target nucleic acid molecule, said first binding material is a reporter probe selected to hybridize with a portion of said target nucleic acid molecule, and said second binding material is a capture probe selected to hybridize with a portion of said target nucleic acid molecule other than the portion of said target nucleic acid molecule for which said reporter probe is selected.

15. The method according to claim 14, wherein said target nucleic acid molecule is found in an organism selected from the group consisting of bacteria, fungi, viruses, protozoa, parasites, animals, and plants.

16. The method according to claim 1, wherein said particle is selected from the group consisting of liposomes, latex beads, gold particles, silica particles, dendrimers, quantum dots, and magnetic beads.

17. The method according to claim 16, wherein said particle is a liposome, said marker is encapsulated in said liposome, and said method further comprises lysing said liposome following said contacting and before said detecting.

18. The method according to claim 1, wherein said marker comprises an electroactive marker.

19. The method according to claim 18, wherein said electroactive marker is a reversible redox couple.

20. The method according to claim 18, wherein said detection assembly is an electrochemical detection assembly.

21. The method according to claim 20, wherein said electrochemical detection assembly comprises an electrode array comprising a first conductor having a plurality of fingers and a second conductor having a plurality of fingers, wherein said fingers of said first conductor are interdigitated with said fingers of said second conductor, said first and second conductors are electrically connected to one another via a voltage source and readout device, and said array is positioned to induce redox cycling of the electroactive marker.

22. The method according to claim 1, wherein said marker comprises an optical marker.

23. The method according to claim 22, wherein said detection assembly is an optical detection assembly.

* * * * *

SEQUENCE LISTING

<160> NUMBER OF SEQ ID NOS: 23

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Generic 20 nt liposome probe

<400> SEQUENCE: 1
ccacccccac ccccaccccc                    20

<210> SEQ ID NO 2
<211> LENGTH: 39

-continued

```
<212> TYPE: DNA
<213> ORGANISM: Artificial Sequence
<220> FEATURE:
<223> OTHER INFORMATION: Description of Artificial Sequence: E. coli
      specific reporter probe

<400> SEQUENCE: 2
gtctggtgaa ttggttccgg ggggtggggg tgggggtgg                              39

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: E. coli
      specific reporter probe

<400> SEQUENCE: 3
gtctggtgaa ttggttcc                                                     18

<210> SEQ ID NO 4
<211> LENGTH: 40
<212> TYPE: DNA
<213> ORGANISM: Artificial Sequence
<220> FEATURE:
<223> OTHER INFORMATION: Description of Artificial Sequence: C. parvum
      specific reporter probe

<400> SEQUENCE: 4
gtgcaacttt agctccagtt gggggtgggg gtgggggtgg                             40

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic
      E. coli target sequence

<400> SEQUENCE: 5
ggcaaccgtg tcgtttatca gaccacttaa ccaaggc                                37

<210> SEQ ID NO 6
<211> LENGTH: 97
<212> TYPE: DNA
<213> ORGANISM: Artificial Sequence
<220> FEATURE:
<223> OTHER INFORMATION: Description of Artificial Sequence: Synthetic
      C. parvum target sequence

<400> SEQUENCE: 6
accagcatcc ttgagcattt tctcaactgg agctaaagtt gcacggaagt aatcagcgca       60
gagttcttcg aatctagctc tactgatggc aactgaa                                97

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: E. coli
      specific capture probe

<400> SEQUENCE: 7
ccgttggcac agcaaata                                                     18

<210> SEQ ID NO 8
```

```
<211> LENGTH: 20
<212> TYPE: DNA
<213> ORGANISM: Artificial Sequence
<220> FEATURE:
<223> OTHER INFORMATION: Description of Artificial Sequence:  C. parvum
      specific capture probe

<400> SEQUENCE: 8
agattcgaag aactctgcgc                                              20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence:  C. parvum
      reporter probe

<400> SEQUENCE: 9
gtgcaacttt agctccagtt                                              20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence:  B.
      anthracis reporter probe

<400> SEQUENCE: 10
caagatgtcc gcgtatttat                                              20

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence:  17 nt
      reporter probe

<400> SEQUENCE: 11
gtctggtgaa ttggttccgg gggtgggggt ggggg                             35

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence:  Liposome
      probe

<400> SEQUENCE: 12
cccccacccc caccccc                                                 17

<210> SEQ ID NO 13
<211> LENGTH: 38
<212> TYPE: DNA
<213> ORGANISM: Artificial Sequence
<220> FEATURE:
<223> OTHER INFORMATION: Description of Artificial Sequence:  20 nt
      reporter probe

<400> SEQUENCE: 13
gtctggtgaa ttggttccgg gggtgggggt ggggtgg                           38

<210> SEQ ID NO 14
<211> LENGTH: 43
```

-continued

<212> TYPE: DNA
<213> ORGANISM: Artificial Sequence
<220> FEATURE:
<223> OTHER INFORMATION: Description of Artificial Sequence: 25 nt
reporter probe

<400> SEQUENCE: 14
gtctggtgaa ttggttccgg gggtgggggt gggggtgggg gtg 43

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Liposome
probe

<400> SEQUENCE: 15
cacccccacc cccaccccca ccccc 25

<210> SEQ ID NO 16
<211> LENGTH: 48
<212> TYPE: DNA
<213> ORGANISM: Artificial Sequence
<220> FEATURE:
<223> OTHER INFORMATION: Description of Artificial Sequence: 30 nt
reporter probe

<400> SEQUENCE: 16
gtctggtgaa ttggttccgg gggtgggggt gggggtgggg gtgggggt 48

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence: Liposome
probe

<400> SEQUENCE: 17
acccccaccc ccacccccac ccccaccccc 30

<210> SEQ ID NO 18
<211> LENGTH: 43
<212> TYPE: DNA
<213> ORGANISM: Artificial Sequence
<220> FEATURE:
<223> OTHER INFORMATION: Description of Artificial Sequence: Synthetic
atxA target sequence

<400> SEQUENCE: 18
ataaatacgc ggacatcttg tcttctcttc ccgatatttc tag 43

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Capture
probe

<400> SEQUENCE: 19
ctagaaatat cgggaagaga a 21

<210> SEQ ID NO 20
<211> LENGTH: 41
<212> TYPE: DNA

-continued

```
<213> ORGANISM: Artificial Sequence
<220> FEATURE:
<223> OTHER INFORMATION: Description of Artificial Sequence:   Reporter
      probe

<400> SEQUENCE: 20
caagatgtcc gcgtatttat gggggtggg ggtgggggtg g                          41

<210> SEQ ID NO 21
<211> LENGTH: 97
<212> TYPE: DNA
<213> ORGANISM: Artificial Sequence
<220> FEATURE:
<223> OTHER INFORMATION: Description of Artificial Sequence:   Synthetic
      hsp 70 target sequence

<400> SEQUENCE: 21
accagcatcc ttgagcattt tctcaactgg agctaaagtt gcacggaagt aatcagcgca    60
gagttcttcg aatctagctc tactgatggc aactgaa                             97

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence:   Capture
      probe

<400> SEQUENCE: 22
agattcgaag aactctgcgc                                                20

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence:   Reporter
      probe

<400> SEQUENCE: 23
gtgcaacttt agctccagtt ggggtgggg gtggggtgg                            40
```